(12) United States Patent
Onik et al.

(10) Patent No.: US 11,612,426 B2
(45) Date of Patent: Mar. 28, 2023

(54) IMMUNOLOGIC TREATMENT OF CANCER

(71) Applicant: ImmunSYS, Inc., Fort Lauderdale, FL (US)

(72) Inventors: Gary Onik, Fort Lauderdale, FL (US); James A. Miessau, Branford, CT (US); DG Bostwick, Orlando, FL (US)

(73) Assignee: ImmunSys, Inc., Fort Lauderdale, FL (US)

( * ) Notice: Subject to any disclaimer, the term of this patent is extended or adjusted under 35 U.S.C. 154(b) by 184 days.

(21) Appl. No.: 16/070,072

(22) PCT Filed: Jan. 13, 2017

(86) PCT No.: PCT/US2017/013486
§ 371 (c)(1),
(2) Date: Jul. 13, 2018

(87) PCT Pub. No.: WO2017/123981
PCT Pub. Date: Jul. 20, 2017

(65) Prior Publication Data
US 2019/0023804 A1  Jan. 24, 2019

Related U.S. Application Data

(60) Provisional application No. 62/279,579, filed on Jan. 15, 2016.

(51) Int. Cl.
| | |
|---|---|
| *A61K 38/19* | (2006.01) |
| *A61K 39/395* | (2006.01) |
| *C07K 16/28* | (2006.01) |
| *A61B 18/00* | (2006.01) |
| *A61B 18/14* | (2006.01) |
| *A61N 1/32* | (2006.01) |
| *A61B 18/02* | (2006.01) |
| *A61P 35/00* | (2006.01) |
| *A61K 45/06* | (2006.01) |

(52) U.S. Cl.
CPC .............. *A61B 18/14* (2013.01); *A61B 18/02* (2013.01); *A61K 38/193* (2013.01); *A61K 39/39558* (2013.01); *A61N 1/327* (2013.01); *A61P 35/00* (2018.01); *C07K 16/2818* (2013.01); *C07K 16/2863* (2013.01); *C07K 16/2878* (2013.01); *C07K 16/2896* (2013.01); *A61B 2018/00577* (2013.01); *A61B 2018/00994* (2013.01); *A61B 2018/0293* (2013.01); *A61K 45/06* (2013.01); *A61K 2300/00* (2013.01)

(58) Field of Classification Search
None
See application file for complete search history.

(56) References Cited

U.S. PATENT DOCUMENTS

| | | |
|---|---|---|
| 4,483,338 A | 11/1984 | Bloom |
| 5,139,496 A | 8/1992 | Hed et al. |
| 5,575,811 A | 11/1996 | Reid |
| 5,672,174 A | 9/1997 | Gough et al. |
| 5,931,807 A | 8/1999 | McClure |
| 6,120,493 A | 9/2000 | Hofmann |
| 6,135,990 A | 10/2000 | Heller et al. |
| 6,214,297 B1 | 4/2001 | Zhang et al. |
| 6,241,702 B1 | 6/2001 | Lundquist |
| 6,379,348 B1 * | 4/2002 | Onik ................. A61B 18/02 606/21 |
| 6,408,199 B1 | 6/2002 | Goldin |
| 6,482,619 B1 | 11/2002 | Rubisky et al. |
| 6,505,629 B1 | 1/2003 | Mikus et al. |
| 6,575,969 B1 | 6/2003 | Rittman, III et al. |
| 6,623,480 B1 | 9/2003 | Kuo et al. |
| 6,733,485 B1 | 5/2004 | Whitehurst et al. |
| 6,978,174 B2 | 12/2005 | Gelfand et al. |
| 7,113,821 B1 | 9/2006 | Sun et al. |
| 7,162,303 B2 | 1/2007 | Levin et al. |
| 7,572,623 B2 | 8/2009 | Mangano et al. |
| 7,620,451 B2 | 11/2009 | Demarais et al. |
| 7,653,438 B2 | 1/2010 | Deem et al. |
| 7,680,543 B2 | 3/2010 | Azure |
| 7,744,878 B2 | 6/2010 | Mather |
| 7,853,333 B2 | 12/2010 | Demarais |
| 7,937,143 B2 | 5/2011 | Demarais et al. |
| 7,938,824 B2 | 5/2011 | Chomenky |
| 8,048,067 B2 | 11/2011 | Davalos et al. |

(Continued)

FOREIGN PATENT DOCUMENTS

| | | |
|---|---|---|
| CN | 103118678 | 5/2013 |
| JP | 2001523987 | 11/2001 |

(Continued)

OTHER PUBLICATIONS

Zhu et al. Cell (2015) 161: 1280-1292.*
Chang et al. (2015) Angew. Chem. Int. Ed., 54, 11760-11764.*
Yu et al. (2014) Oncotarget, vol. 5, No. 15, 6526-6539.*
Rosenberg et. al. (2015) Journal for ImmunoTherapy of Cancer 2015, 3(Suppl 2): P142.*
U.S. Appl. No. 17/101,434, filed Nov. 2020, Onik; Gary.*
Immuno-Oncology News (2015), 2 pages.*
Ito et al. (2015) PLoS ONE 10(11): e0143370. https://doi.org/10.1371/journal.pone.0143370; 23 pages.*

(Continued)

*Primary Examiner* — Ilia I Ouspenski
(74) *Attorney, Agent, or Firm* — Fish & Richardson P.C.

(57) ABSTRACT

Provided herein are new compositions, methods, and devices to treat cancer through a combination of immunologic chemotherapeutic agents and ablation techniques. These compositions can include immune checkpoint inhibitors, cytokines and nucleic acid drugs that aid in eliciting an immune response to treat the tumor. The administration of these compositions in addition to various ablating techniques provides a presentation of the cancer cell antigens to the immune system and the immunologic targeting of the cancer.

28 Claims, 10 Drawing Sheets

(56) References Cited

U.S. PATENT DOCUMENTS

| | | |
|---|---|---|
| 8,114,070 B2 | 2/2012 | Rubinsky et al. |
| 8,131,371 B2 | 3/2012 | Demarais et al. |
| 8,145,316 B2 | 3/2012 | Deem et al. |
| 8,221,411 B2 | 7/2012 | Francischelli et al. |
| 8,226,648 B2 | 7/2012 | Paul et al. |
| 8,231,603 B2 | 7/2012 | Hobbs et al. |
| 8,282,631 B2 | 10/2012 | Davalos et al. |
| 8,465,484 B2 | 6/2013 | Davalos et al. |
| 8,814,860 B2 | 8/2014 | Davalos et al. |
| 9,545,523 B2 | 1/2017 | Nanda |
| 9,598,491 B2* | 3/2017 | Ahmed ..................... A61P 1/16 |
| 10,154,869 B2 | 12/2018 | Onik et al. |
| 10,448,989 B2 | 10/2019 | Arena et al. |
| 10,849,678 B2* | 12/2020 | Onik ..................... A61N 1/325 |
| 11,141,216 B2 | 10/2021 | Onik et al. |
| 11,497,544 B2* | 11/2022 | Onik ..................... A61B 18/02 |
| 2001/0044596 A1 | 11/2001 | Jaafar |
| 2002/0019644 A1 | 2/2002 | Hastings et al. |
| 2002/0086014 A1* | 7/2002 | Korman ............ A01K 67/0276<br>424/144.1 |
| 2002/0087151 A1 | 7/2002 | Mody et al. |
| 2002/0095124 A1 | 7/2002 | Palasis et al. |
| 2002/0111617 A1 | 8/2002 | Cosman et al. |
| 2002/0128640 A1 | 9/2002 | Swanson et al. |
| 2002/0183684 A1 | 12/2002 | Dev et al. |
| 2002/0193784 A1 | 12/2002 | McHale et al. |
| 2002/0193789 A1 | 12/2002 | Underwood et al. |
| 2003/0018329 A1 | 1/2003 | Hooven |
| 2003/0045495 A1* | 3/2003 | Li ..................... A61K 48/0058<br>514/44 R |
| 2003/0055471 A1 | 3/2003 | Fenn et al. |
| 2003/0093067 A1 | 5/2003 | Panescu |
| 2003/0153960 A1 | 8/2003 | Chornenky |
| 2003/0163040 A1 | 8/2003 | Gildenberg |
| 2003/0204161 A1 | 10/2003 | Ferek-Petric |
| 2003/0216722 A1 | 11/2003 | Swanson et al. |
| 2003/0216792 A1 | 11/2003 | Levin et al. |
| 2004/0143261 A1 | 7/2004 | Hartley et al. |
| 2004/0248842 A1* | 12/2004 | Wagner ................. C08G 81/00<br>514/44 R |
| 2005/0038422 A1 | 2/2005 | Maurice et al. |
| 2005/0182462 A1 | 8/2005 | Chornenky et al. |
| 2005/0214268 A1 | 9/2005 | Cavanagh et al. |
| 2005/0221270 A1 | 10/2005 | Connelly et al. |
| 2005/0261672 A1 | 11/2005 | Deem |
| 2005/0288667 A1 | 12/2005 | Thompson et al. |
| 2005/0288730 A1 | 12/2005 | Deem et al. |
| 2006/0041277 A1 | 2/2006 | Deem et al. |
| 2006/0073589 A1* | 4/2006 | Belardelli ............ C12N 5/0645<br>435/372 |
| 2006/0149147 A1 | 7/2006 | Yanof |
| 2006/0161246 A1 | 7/2006 | Rhim et al. |
| 2006/0293725 A1 | 12/2006 | Rubinsky et al. |
| 2006/0293730 A1 | 12/2006 | Rubinsky et al. |
| 2007/0031338 A1* | 2/2007 | Zabinski ............ A61K 49/226<br>424/9.6 |
| 2007/0043345 A1 | 2/2007 | Davalos et al. |
| 2007/0049919 A1 | 3/2007 | Lee |
| 2007/0060989 A1 | 3/2007 | Deem |
| 2007/0066957 A1 | 3/2007 | Demarais et al. |
| 2007/0083193 A1 | 4/2007 | Werneth et al. |
| 2007/0083239 A1 | 4/2007 | Demarais et al. |
| 2007/0129720 A1 | 6/2007 | Demarais et al. |
| 2007/0129760 A1 | 6/2007 | Demarais |
| 2007/0233057 A1 | 10/2007 | Konishi |
| 2008/0033417 A1 | 2/2008 | Nields et al. |
| 2008/0058706 A1 | 3/2008 | Zhang et al. |
| 2008/0071265 A1 | 3/2008 | Azure |
| 2008/0132884 A1 | 6/2008 | Rubinsky et al. |
| 2008/0132885 A1 | 6/2008 | Rubinsky et al. |
| 2008/0208052 A1 | 8/2008 | LePivert et al. |
| 2008/0247506 A1 | 10/2008 | Maschke |
| 2008/0306476 A1 | 12/2008 | Hennings et al. |
| 2008/0319375 A1 | 12/2008 | Hardy |
| 2009/0028857 A1* | 1/2009 | Li .................... A61K 39/39558<br>424/133.1 |
| 2009/0088648 A1 | 4/2009 | Jaffe et al. |
| 2009/0118727 A1 | 5/2009 | Pearson et al. |
| 2009/0143717 A1 | 6/2009 | Bass |
| 2009/0177094 A1 | 7/2009 | Brown et al. |
| 2009/0292342 A1 | 11/2009 | Rubinsky et al. |
| 2009/0326366 A1 | 12/2009 | Krieg |
| 2010/0023004 A1 | 1/2010 | Francischelli et al. |
| 2010/0030211 A1 | 2/2010 | Davalos et al. |
| 2010/0049031 A1 | 2/2010 | Fruland et al. |
| 2010/0049178 A1 | 2/2010 | Deem |
| 2010/0069833 A1 | 3/2010 | Wenderow et al. |
| 2010/0100092 A1 | 4/2010 | Turner et al. |
| 2010/0152725 A1 | 6/2010 | Pearson et al. |
| 2010/0179530 A1 | 7/2010 | Long et al. |
| 2010/0221351 A1* | 9/2010 | He ....................... A61K 31/568<br>424/493 |
| 2010/0249771 A1 | 9/2010 | Pearson et al. |
| 2010/0250209 A1 | 9/2010 | Pearson et al. |
| 2010/0261944 A1 | 10/2010 | Davalos et al. |
| 2010/0262067 A1 | 10/2010 | Chomenky et al. |
| 2010/0274178 A1 | 10/2010 | LePivert et al. |
| 2010/0331758 A1 | 12/2010 | Davalos et al. |
| 2011/0015630 A1 | 1/2011 | Azure |
| 2011/0082534 A1 | 4/2011 | Wallace |
| 2011/0106221 A1 | 5/2011 | Neal, II et al. |
| 2011/0112520 A1 | 5/2011 | Michael |
| 2011/0160514 A1 | 6/2011 | Long et al. |
| 2011/0160614 A1 | 6/2011 | Fujiwara et al. |
| 2011/0166499 A1 | 7/2011 | Demarais et al. |
| 2011/0190659 A1 | 8/2011 | Long et al. |
| 2011/0190764 A1 | 8/2011 | Long et al. |
| 2011/0202053 A1 | 8/2011 | Moss et al. |
| 2011/0217270 A1* | 9/2011 | Cavanagh, III .... A61K 39/0011<br>424/93.7 |
| 2012/0021481 A1 | 1/2012 | Hebner et al. |
| 2012/0041525 A1 | 2/2012 | Kami |
| 2012/0071749 A1 | 3/2012 | Xu et al. |
| 2012/0071872 A1 | 3/2012 | Rubinsky et al. |
| 2012/0071874 A1 | 3/2012 | Davalos et al. |
| 2012/0109122 A1 | 5/2012 | Arena et al. |
| 2012/0143181 A1 | 6/2012 | Demarais et al. |
| 2012/0190040 A1 | 7/2012 | Talebpour et al. |
| 2012/0215218 A1 | 8/2012 | Lipani |
| 2012/0215221 A1 | 8/2012 | Woloszko |
| 2012/0220998 A1 | 8/2012 | Long et al. |
| 2012/0220999 A1 | 8/2012 | Long |
| 2012/0221002 A1 | 8/2012 | Long et al. |
| 2012/0230939 A1* | 9/2012 | Perambakam .......... A61P 35/00<br>424/85.1 |
| 2012/0252087 A1 | 10/2012 | Hebner et al. |
| 2012/0253188 A1 | 10/2012 | Holland |
| 2012/0277741 A1 | 11/2012 | Davalos et al. |
| 2012/0277763 A1 | 11/2012 | Greenblatt |
| 2013/0108667 A1 | 3/2013 | Wang et al. |
| 2013/0101551 A1* | 4/2013 | Har-Noy ................ A61K 38/21<br>424/85.2 |
| 2013/0071905 A1 | 5/2013 | Soikum et al. |
| 2013/0110098 A1 | 5/2013 | Lalonde |
| 2013/0184702 A1 | 7/2013 | Neal, II et al. |
| 2013/0189301 A1 | 7/2013 | Har-Noy |
| 2013/0211230 A1 | 8/2013 | Sperling |
| 2013/0237984 A1 | 9/2013 | Sklar |
| 2013/0289369 A1 | 10/2013 | Margolis |
| 2013/0295110 A1 | 11/2013 | Binder et al. |
| 2013/0302409 A1 | 11/2013 | Fuchs et al. |
| 2013/0304062 A1 | 11/2013 | Chan et al. |
| 2013/0310823 A1 | 11/2013 | Gefland et al. |
| 2013/0345697 A1 | 12/2013 | Garcia et al. |
| 2014/0012251 A1 | 1/2014 | Himmelstein et al. |
| 2014/0039491 A1 | 2/2014 | Basok et al. |
| 2014/0088578 A1 | 3/2014 | Rubinsky et al. |
| 2014/0172054 A1 | 6/2014 | Zarins et al. |
| 2014/0205609 A1* | 7/2014 | Valentine ........... A61K 39/0011<br>424/142.1 |
| 2014/0234296 A1* | 8/2014 | Sharma ............ A61K 39/39591<br>424/133.1 |
| 2014/0257272 A1 | 9/2014 | Clark et al. |

(56) References Cited

U.S. PATENT DOCUMENTS

| | | | |
|---|---|---|---|
| 2014/0328833 A1 | 11/2014 | Korman et al. | |
| 2014/0350537 A1 | 11/2014 | Baust et al. | |
| 2014/0356397 A1 | 12/2014 | Akle et al. | |
| 2015/0150618 A1* | 6/2015 | Onik | A61B 18/00 606/41 |
| 2015/0190505 A1* | 7/2015 | Yeung | A61K 39/235 424/135.1 |
| 2015/0201996 A1 | 7/2015 | Rubisky | |
| 2015/0230850 A1 | 8/2015 | McKay | |
| 2015/0265705 A1* | 9/2015 | Li | A61K 39/39558 424/9.2 |
| 2015/0374436 A1 | 12/2015 | Subramaniam et al. | |
| 2016/0128767 A1 | 5/2016 | Azamian et al. | |
| 2016/0338754 A1* | 11/2016 | Baust | F25B 19/005 |
| 2016/0346354 A1* | 12/2016 | Heslet | A61P 31/00 |
| 2016/0367310 A1 | 12/2016 | Onik et al. | |
| 2017/0020931 A1 | 1/2017 | Zhou et al. | |
| 2017/0143780 A1* | 5/2017 | Zitvogel | A61K 39/3955 |
| 2017/0274011 A1* | 9/2017 | Garibyan | A61P 17/00 |
| 2018/0021084 A1 | 1/2018 | Onik et al. | |
| 2018/0028260 A1 | 2/2018 | Onik et al. | |
| 2018/0028267 A1 | 2/2018 | Onik et al. | |
| 2018/0133319 A1* | 5/2018 | Vo-Dinh | A61K 9/51 |
| 2018/0154142 A1* | 6/2018 | Guo | A61K 45/00 |
| 2018/0263685 A1 | 9/2018 | Onik et al. | |
| 2018/0318365 A1* | 11/2018 | Yeung | C07K 16/2818 |
| 2018/0318393 A1* | 11/2018 | Pierce | A61K 48/0091 |
| 2019/0183561 A1 | 6/2019 | Hobbs et al. | |
| 2019/0209652 A1* | 7/2019 | Pierce | A61P 35/00 |
| 2019/0241658 A1 | 8/2019 | Frederick | C07K 16/2818 |
| 2019/0298770 A1* | 10/2019 | Rabinovich | A61K 35/17 |
| 2020/0038093 A1* | 2/2020 | Onik | A61N 1/325 |
| 2020/0040095 A1* | 2/2020 | Onik | A61P 35/00 |
| 2020/0277379 A1* | 9/2020 | Bostwick | A61K 31/675 |
| 2021/0177491 A1 | 6/2021 | Onik et al. | |
| 2022/0257761 A1* | 8/2022 | Bostwick | A61K 38/212 |

FOREIGN PATENT DOCUMENTS

| | | |
|---|---|---|
| JP | 2006187446 | 7/2006 |
| JP | 2009297527 | 12/2009 |
| JP | 2010500153 | 1/2010 |
| JP | 2013531043 | 8/2013 |
| JP | 5341287 | 11/2013 |
| JP | 2015-38492 A | 2/2015 |
| WO | WO 2004/037313 | 5/2004 |
| WO | WO 2008/034103 | 3/2008 |
| WO | WO 2010/080974 | 7/2010 |
| WO | WO 2012/088149 | 6/2012 |
| WO | WO 2012/099974 | 7/2012 |
| WO | WO 2013/053775 | 4/2013 |
| WO | WO 2013/079980 | 6/2013 |
| WO | WO 2014/149690 | 9/2014 |
| WO | WO 2015/085162 | 6/2015 |
| WO | WO 2015/125159 | 8/2015 |
| WO | WO 2015/140150 | 9/2015 |
| WO | WO 2015/153639 | 10/2015 |
| WO | WO 2016/123608 | 8/2016 |
| WO | WO 2016/126778 | 8/2016 |
| WO | WO 2016/126811 | 8/2016 |
| WO | WO 2016/126905 | 8/2016 |
| WO | WO 2016/127162 | 8/2016 |
| WO | WO 2017/123981 | 7/2017 |

OTHER PUBLICATIONS

Waitz et al. (2012) Cancer Res; 72(2); 430-439.*
Waitz et al. (2012) OncoImmunology, 1:4, 544-546.*
Mizukoshi et al. (2013) Hepatology 57: 1448-1457.*
Bastianpillai et al. (2015) Tumor Biol. 36: 9137-9146.*
Au et al. (2013) Surgery 154: 496-503.*
Shi et al. (2016) Clin Cancer Res; 22(5): 1173-1184.*
Bulvik et al. (2016) Radiology: vol. 280, No. 2, 413-424.*
Paiella et al. (2016) Gastroenterology Research and Practice, vol. 2016, Article ID 4508376, 10 pages.*
Carosella et al. (2015) European Urology 68: 267-279.*
Onik et al. Regression of metastatic cancer and abscopal effects following in situ vaccination by cryosurgical tumor cell lysis and intratumoral immunotherapy: A case series. Cancer Res 2020; 80(16 Suppl): Abstr. 6540 (4 pages).*
JP Office Action in Japanese Appln. No. 2018-555838, dated Jan. 26, 2021, 8 pages (with English translation).
EP Extended Search Report in European Appln. No. 17739066.3, dated Dec. 16, 2019, 20 pages.
European Search Report in European Application. No. 17739066, dated Aug. 13, 2019, 23 pages.
Brooks et al., "Intratumoral injection of GM-CSF in perspective—a review," J Medi., Jan. 1, 2003, 34(1-6):149-153.
Fehres et al., "Understanding the Biology of Antigen Cross-Presentation for the Design of Vaccines Against Cancer," Frontiers in Immunology, Apr. 8, 2014, 5(149):1-10.
Hebb Jonathan et al., "Systemic Antitumor Effects of Intratumoral Administration of the Novel Immunotherapeutic Combination Anti-CTLA4, Anti-CD137, and Anti-OX40 in Mouse Models of Lymphoma and Solid Tumor," Blood, Jan. 1, 2015, 126(23):1552.
Koster et el., "Recent developments and future challenges in immune checkpoint inhibitory cancer treatment," Curr Opin Oncol., Nov. 2015, 27(6):482-488.
AMGen.com, "FDA Approves IMLYGIC™ (Talimogene Laherparepvec) As First Oncolytic Viral Therapy In The US," retrieved Aug. 13, 2020 from URL <https://www.amgen.com/media/news-releases/2015/10/fda-approves-imlygic-talimogene-laherparepvec-as-first-oncolytic-viral-therapy-in-the-us/>, Oct. 27, 2015, 7 pages.
PRNewswire.com, "Image Guided Cancer Specialists Reports Successful Early Results from Cryoablation and Intra-tumoral Injection of Immunotherapy Drug Combination Yerivoy and Keytruda for the Treatment of Cancer," retrieved Jul. 15, 2020 from URL <https://www.prnewswire.com/news-releases/image-guided-cancer-specialists-reports-successful-early-results-from-cryoablation-and-intra-tumoral-injection-of-immunotherapy-drug-combination-yerivoy-and-keytruda-for-the-treatment-of-cancer-300029347.html>, Feb. 23, 2015, 4 pages.
Arora et al., "Neoadjuvant Intratumoral Cytokine-Loaded Microspheres are Superior to Postoperative Autologous Cellular Vaccines in Generating Systematic Anti-Tumor Immunity," J. Surgical Oncology 94(5):403-412, dated Oct. 1, 2006.
International Preliminary Report on Patentability in International Application No. PCT/US2017/013486, dated Jul. 17, 2018, 33 pages.
International Search Report and Written Opinion in International Application No. PCT/US2017/013486, dated May 19, 2017, 38 pages.
Somasundaram et al., "Nivolumab in Combination with Ipilimumab for the Treatment of Melanoma. Expert Rev. Anti-Cancer Therapy," 15(10):1-13, dated Oct. 2015.
Wang et al., "In Vitro Characterization of the Anti-PD-1 Antibody Nivolumab, BMS-936558, and In Vivo Toxicology in Non-Human Primates," Cancer Immunology Research 2(9):846-856, dated May 28, 2014.
Woolley et al., "Effect of Freezing Parameters (Freeze Cycle and Thaw Process) on Tissue Destruction Following Renal Cryoablation," Journal of Endourology 16(7):519-522, dated Sep. 2002.
Aarts et al., "Cryoablation and immunotherapy: an overview of evidence on its synergy," Insights Into Imaging, Dec. 2019, 10(1), 12 pages.
Abdo et al., "Immunotherapy plus cryotherapy: potential augmented abscopal effect for advanced cancers," Frontiers in Oncology, Mar. 28, 2018, 8:85.
Al Sakere et al., "A study of the immunological response to tumor ablation with irreversible electroporation," Technol Cancer Res Treat, Aug. 2007, 6(4):301-306.
Ammar et al., "Impact of a pulsed electric field on damage of plant tissues: effects of cell size and tissue electrical conductivity," J Food Sci., Jan.-Feb. 2011, 76(1):E90-7.
Arena et al. "High-Frequency Irreversible Electroporation (H-FIRE) for Non-Thermal Ablation without Muscle Contraction", Biomed Eng. Online Nov. 21, 2011, 10:102.

(56) References Cited

OTHER PUBLICATIONS

Aronsson et al., "Inactivation of *Escherichia coli*, Listeria innocua and *Saccharomyces cerevisiae* in relation to membrane permeabilization and subsequent leakage of intracellular compounds due to pulsed electric field processing," Int J Food Microbiol., Mar. 1, 2005, 99(1):19-32.

Asavasanti et al., "Critical electric field strengths of onion tissues treated by pulsed electric fields," J Food Sci., Sep. 2010, 75(7):E433-43.

Asavasanti et al., "Permeabilization of plant tissues by monopolar pulsed electric fields: effect of frequency," J Food Sci. Jan-Feb. 2011, 76(1):E98-111.

Barnett et al., "Surgical ablation as treatment for the elimination of atrial fibrillation: a meta-analysis," The Journal of thoracic and cardiovascular surgery, May 1, 2006, 131(5):1029-35.

Beebe et al., "Non-ionizing radiation with nanosecond pulsed electric fields as a cancer treatment: in vitro studies," Conf Proc IEEE Eng Med Biol Soc., Sep. 2-6, 2009, pp. 6509-6512.

Bertacchini et al., "Design of an irreversible electroporation system for clinical use," Technol Cancer Res Treat., Aug. 2007, 6(4):313-20.

Chang et al. "Changes in Membrane Structure Induced by Electroporation as Revealed by Rapid-Freezing Electron Microscopy", Biophys J., Jul. 1, 1990, 58(1):1-12.

Chang et al., "Construction of a Genomic Map of H. pylori by Pulsed-Field Gel Electrophoresis (PFGE)," Methods Mol Med., 1997, 8:165-176.

Chen et al., "Leukemic cell intracellular responses to nanosecond electric fields," Biochem Biophys Res Commun., Apr. 30, 2004, 317(2):421-427.

Chen et al., "Membrane electroporation theories: a review," Med Biol Eng Comput., 2006, 44:5-14.

Chen et al., "Nanosecond electric pulses penetrate the nucleus and enhance speckle formation," Biochem Biophys Res Commun., Dec. 14, 2007, 364(2):220-225.

Chen et al., "Picosecond pulsed electric fields induce apoptosis in HeLa cells via the endoplasmic reticulum stress and caspase-dependent signaling pathways," Int J Oncol., Mar. 2013, 42(3):963-70.

Cox et al,. "The surgical treatment of atrial fibrillation," The Journal of thoracic and cardiovascular surgery. 1991, 101(1-4):402-426, 569-592.

Crowley "Electrical breakdown of bimolecular lipid membranes as an electromechanical instability," Biophys J., Jul. 1973, 13(7):711-724.

Cummings et al., "Alternative energy sources for the ablation of arrhythmias," Pacing and clinical electrophysiology, May 2005, 28(5):434-43.

Djunzenova et al., "Effect of electric field pulses on the viability and on the membrane-bound immunoglobulins of LPS-activated murine B-lymphocytes: correlation with the cell cycle," Cymetry, Jan. 1, 1994, 15(1):35-45.

Doll et al., "Esophageal perforation during left atrial radiofrequency ablation: is the risk too high?," The Journal of Thoracic and Cardiovascular Surgery, Apr. 1, 2003, 125(4):836-42.

Dortch et al., "Characterization of pulsed magnetic field therapy in a rat model for rheumatoid arthritis," Biomed Sci Instrum., 2006, 42:302-307, Abstract Only.

Dyson et al., "Kinetic and physical studies of cell death induced by chemotherapeutic agents or hyperthermia," Cell Tissue Kinet., May 1986, 19(3):311-324.

Eppich et al., "Pulsed electric fields for selection of hematopoietic cells and depletion of tumor cell contaminants," Nat Biotechnol., Aug. 2000, 18(8):882-887.

Ersus et al., "Disintegration efficiency of pulsed electric field induced effects on onion (*Allium cepa* L.) tissues as a function of pulse protocol and determination of cell integrity by $^1$H-NMR relaxometry," J Food Sci. Sep. 2010 ,75(7):E444-52.

European Search Report in European Application No. 16744266.4, dated Oct. 18, 2018, 10 pages.

Foltz, "Algae Lysis with Pulsed Electric Fields," California State Polytechnic University, San Luis Obispo 2012, [retrieved on May 13, 2019]retrieved from URL <http://digitalcommons.-calpoly.edu/theses/732/>, 76 pages.

García et al., "Biosynthetic requirements for the repair of sublethal membrane damage in *Escherichia coli* cells after pulsed electric fields," J Appl Microbiol., Mar. 2006, 100(3):428-435.

Garilevich et al., "Outlook for the use of focused shock waves and pulsed electric fields in the complex treatment of malignant neoplasms," Conf Proc IEEE Eng Med Biol Soc. 2006, 1:6370-6372.

Gómez-Ochoa et al., "Pulsed electromagnetic fields decrease proinflammatory cytokine secretion (IL-1 β and TNF-α) on human fibroblast-like cell culture," Rheumatol Int., Oct. 2011, 31(10):1283-1289.

Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, Jun. 1999, 1(2):123-127.

Gordon et al., "Intracellular hyperthermia. A biophysical approach to cancer treatment via intracellular temperature and biophysical alterations," Med Hypotheses., Jan. 1979, 5(1):83-102.

Grys et al., "Decreasing the thresholds for electroporation by sensitizing cells with local cationic anesthetics and substances that decrease the surface negative electric charge," Cell Mol Biol Lett., Mar. 2014, 19(1):65-76.

Hamid et al., "Safety and tumor responses with lambrolizumab (anti-PD-1) in melanoma," N Engl J Med., Jul. 11, 2013, 369(2):134-144.

Harris "Effects of Tumor-like assay conditions, Ionizing radiation, and hyperthermia on immune lysis of tumor cells by cytotoxic T-lymphocytes," Cancer Res., Aug. 1976, 36(8):2733-2739.

Hebb et al., "Systemic Antitumor Effects of Intratumoral Administration of the Novel Immunotherapeutic Combination Anti-CTLA4, Anti-CD137, and Anti-0X40 in Mouse Models of Lymphoma and Solid Tumor," Blood Journal, Dec. 3, 2015 126(23):1552.

Hillen et al., "Treatment of Metastatic Posterior Vertebral Body Osseous Tumors by Using a Targeted Bipolar Radiofrequency Ablation Device: Technical Note," Radiology, Jun. 13, 2014, 273(1):261-267.

Hua et al., "Intense picosecond pulsed electric fields induce apoptosis through a mitochondrial-mediated pathway in HeLa cells," Mol Med Rep., Apr. 2012, 5(4):981-987.

Iu et al., "Reduction in levels of *Escherichia coli* O157:H7 in apple cider by pulsed electric fields," J Food Prot., Jul. 2001, 64(7):964-969.

Jaeger et al., "Protective effect of milk constituents and sublethal injuries limiting process effectiveness during PEF inactivation of Lb. rhamnosus," Int J Food Microbiol., Aug. 31, 2009, 134(1-2):154-161.

Jeffers et al., "Dimethylformamide as an enhancer of cavitation-induced cell lysis in vitro," J Acoust Soc Am., Jan. 1995, 97(1):669-676.

Jia et al., "Crystal structure of human grancalcin, a member of the penta-EF-hand protein family," J Mol Biol., Jul. 28, 2000, 300(5):1271-81.

Kawano et al., "Cryoimmunologic Antitumor Effects Enhanced by Dendritic Cells in Osteosarcoma", Clin Orthop Relat Res., May 2010, 468(5)1373-1383.

Kennedy et al., "Cationic Peptide Exposure Enhances Pulsed-Electric-Field-Mediated Membrane Disruption," PLoS One, Mar. 26, 2014, 9(3):e92528.

Kennedy et al., "Quantification of electroporative uptake kinetics and electric field heterogeneity effects in cells," Biophys J., Jun. 2008, 94(12):5018-5027.

Kim et al., "Changes of apoptosis in tumor tissues with time after irreversible electroporation," Biochem Biophys Res Commun., Jun. 14, 2013, 435(4):651-656.

Koga et al., "Interstitial Radiofrequency Hyperthermia for Brain Tumors," Neurol Med Chir., May 1993, 33(5):290-294.

Laufer et al., "Tissue Characterization Using Electrical Impedance Spectroscopy Data: A Linear Algebra Approach," Physiol Measu., 2012, 33:997-1013.

(56) References Cited

OTHER PUBLICATIONS

Lee et al., "Electron microscopic demonstration and evaluation of irreversible electroporation-induced nanopores on hepatocyte membranes," J Vasc Interv Radiol., Jan. 2012, 23(1)107-113.

Li et al., "Immunologic Response to Tumor Ablation with Irreversible Electroporation", PLOS One, Nov. 6, 2012, 7(11):e48749.

Li et al., "The effect of lipid molecular packing stress on cationic liposome-induced rabbit erythrocyte fusion," Biochim Biophys Acta., Jan. 14, 1997, 1323(1)105-116.

Lin et al., "Preparation of antioxidant peptide from egg white protein and improvement of its activities assisted by high-intensity pulsed electric field," J Sci Food Agric., May 2012, 92(7):1554-1561.

Ma et al., "Experimental Study on Residual Tumor Angiogenesis after Cryoablation," Asian Pac J Cancer Prev., 2014, 15(6):2491-2494.

Machlenkin et al., "Combined dendritic cell cryotherapy of tumor induces systemic antimetastatic immunity," Clinical Cancer Research, Jul. 1, 2005, 11(13):4955-61.

Maor et al., "Irreversible electroporation attenuates neointimal formation after angioplasty," IEEE Trans Biomed Eng., Sep. 2008, 55(9):2268-2274.

Marabelle et al., "Intratumoral anti-CTLA-4 therapy: enhancing efficacy while avoiding toxicity," Clinical Cancer Research, Oct. 1, 2013, 19(19):5261, 4 pages.

Marabelle et al., "Intratumoral immunization: a new paradigm for cancer therapy," Clinical Cancer Research, Apr. 1, 2014, 20(7):1747-56.

Marabelle et al., "Intratumoral immunotherapy: using the tumor as the remedy," Annals of Oncology, Dec. 1, 2017, 28:xii33-43, 11 pages.

Marabelle et al., "Starting the fight in the tumor: expert recommendations for the development of human intratumoral immunotherapy (HIT-IT)," Annals of Oncology, Nov. 1, 2018, 29(11):2163-74.

Marx et al., "A comparative study on the structure of *Saccharomyces cerevisiae* under nonthermal technologies: high hydrostatic pressure, pulsed electric fields and thermo-sonication," Int J Food Microbiol., Dec. 15, 2011, 151(3)327-337.

Mi et al., "[Effect of steep pulsed electric fields on the immune response of tumor-bearing Wistar mice]," Sheng Wu Yi Xue Gong Cheng Xue Za Zhi., Apr. 2007, 24(2):253-256, Abstract Only.

Miller et al., "Integrated Carbon Fiber Electrodes within Hollow Polymer Microneedles for Transdermal Electrochemical Sensing," Biomicrofluidics., Mar. 30, 2011, 5(1):13415.

Miller et al., "Multiplexed microneedle-based biosensor array for characterization of metabolic acidosis," Talanta., Jan. 15, 2012, 88:739-742.

Milligan et al., "Interstitial Hyperthermia," Med Instrum., May-Jun. 1984, 18(3):175-180, Abstract Only.

Mishra et al., "Electric Property Sensing Biopsy Needle for Prostate Cancer Detection," Prostate, Nov. 2013, 73(15):1603-1613.

Morshed et al., "Electrical lysis: dynamics revisited and advances in On-chip operation,"Crit Rev Biomed Eng., 2013, 41(1):37-50.

Neal et al. "In Vitro and Numerical Support for Combinatorial Irreversible Electroporation and Electrochemotherapy Glioma Treatment", Annals of Biomedical Engineering, Mar. 2014, 42(3):475-487.

Neal et al., "Improved local and systemic anti-tumor efficacy for irreversible electroporation in immunocompetent versus immunodeficient mice," PLOS One., May 24, 2013, 8(5):e64559.

Neumann et al., "Permeability changes induced by electric impulses in vesicular membranes," J Membr Biol., Dec. 29, 1972, 10(3):279-290.

Ninet et al., "Surgical ablation of atrial fibrillation with off-pump, epicardial, high-intensity focused ultrasound: results of a multicenter trial," The Journal of thoracic and cardiovascular surgery, Sep. 1, 2005, 130(3):803-809.

O'Dowd et al., "An assessment of the effect of pulsed electrical fields on tenderness and selected quality attributes of post rigour beef muscle," Meat Sci., Feb. 2013, 93(2):303-309.

Onik et al. "Irreversible Electroporation: Implications for Prostate Ablation", Technology in Cancer Res. and Treatment, Aug. 2007, 6(4): 295-300.

Onik et al. "Long-Term Results of Optimized Focal Therapy for Prostate Cancer: Average 10-Year Follow-Up in 70 Patients," Journal of Men's Health, Jun. 2014, 11(2):64-74.

Onik et al., "Three-Dimensional Sonographically Monitoring Cryosurgery in a Prostate Phantom," Journal of Ultrasound, 1996, 16:267-270.

Oshima et al., "Bacterial sterilization and intracellular protein release by a pulsed electric field," Adv Biochem Eng Biotechnol., Adv Biochem Eng Biotechnol., 2004, 90:113-33.

PCT International Preliminary Report on Patentability in International Application No. PCT/US2014/068774, dated Jun. 7, 2016, 13 pages.

PCT International Preliminary Report on Patentability in International Application No. PCT/US2016/015944, dated Aug. 1, 2017, 9 pages.

PCT International Preliminary Report on Patentability in International Application No. PCT/US2016/016300, dated Aug. 8, 2017, 6 pages.

PCT International Preliminary Report on Patentability in International Application No. PCT/US2016/016352, dated Aug. 8, 2017, 6 pages.

PCT International Preliminary Report on Patentability in International Application No. PCT/US2016/016501, dated Aug. 8, 2017, 7 pages.

PCT International Preliminary Report on Patentability in international Appln. No. PCT/US2016/016955, dated Aug. 8, 2017, 6 pages.

PCT International Search Report and Written Opinion in international Appln. No. PCT/US2016/016955, dated Jul. 1, 2016, 9 pages.

PCT International Search Report and Written Opinion in International Application No. PCT/US2014/068774, dated Mar. 19, 2015, 15 pages.

PCT International Search Report and Written Opinion in International Application No. PCT/US2016/015944, dated Jul. 29, 2016, 13 pages.

PCT International Search Report and Written Opinion in International Application No. PCT/US2016/016300, dated Jul. 8, 2016, 9 pages.

PCT International Search Report and Written Opinion in International Application No. PCT/US2016/016352, dated Jul. 18, 2016, 9 pages.

PCT International Search Report and Written Opinion in International Application No. PCT/US2016/016501, dated Sep. 2, 2016, 10 pages.

PCT International Search Report and Written Opinion in PCT Appln. No. PCT/US2019/066876, dated Jun. 2, 2020, 11 pages.

Peper et al., "An impedance-based cytotoxicity assay for real-time and label-free assessment of T-cell-mediated killing of adherent cells," J Immunol Methods, Mar. 2014, 405:192-198.

Persson et al., "A model for evaluating therapeutic response of combined cancer treatment modalities: applied to treatment of subcutaneously implanted brain tumors (N32 and N29) in Fischer rats with pulsed electric fields (PEF) and 60Co-gamma radiation (RT)," Technol Cancer Res Treat., Oct. 1, 2003, 2(5):459-470.

Poudineh et al., "Three-dimensional, sharp-tipped electrodes concentrate applied fields to enable direct electrical release of intact biomarkers from cells," Lab Chip., May 21, 2014, 14(10):1785-1790.

Ribas et al., "Dendritic cell vaccination combined with CTLA4 blockade in patients with metastatic melanoma," Clin Cancer Res., Oct. 1, 2019, 15(19):6267-6275.

Royal, et al., "Phase 2 trial of single agent ipilimumab (anti-CLTA-4) for locally advanced or metastatic pancreatic adenocarcinoma," J. Immunother., 2010, 33(8):828-833.

Sabel et al. "Immunologic Response To Cryoablation Of Breast Cancer," Breast Cancer Research and Treatment, Mar. 2005, 90(1):97-104.

Sabel et al., "Cryo-Immunology: A review of the literature and proposed mechanisms for stumulatory versus suppressive immune responses," Cryobiology, 2009, 58:1-11.

(56) References Cited

OTHER PUBLICATIONS

Sale et al., "Effects of high electric fields on micro-organisms. 3. Lysis of erythrocytes and protoplasts," Biochim Biophys Acta., Aug. 1968, 163(1):37-43.
Schaft et al., "A new way to generate cytolytic tumor-specific T cells: electroporation of RNA coding for a T cell receptor into T lymphocytes," Cancer Immunol Immunother., Sep. 2006,55(9):1132-1141.
Shen et al., "Abstract 4746: Modulation of suppressive myeloid populations by tasquinimod," Cancer Research, Apr. 15, 2013, 73:4746.
Shipman, "Microneedle Sensors May Allow Real-Time Monitoring of Body Chemistry," Dec. 13, 2011, [retrieved on May 15, 2019] retrieved from URL <https://news.ncsu.edu/2011/12/wmsnarayanmnsensors/>, 3 pages.
Sidana, "Cancer immunotherapy using tumor cryoablation," Immunotherapy, Jan. 2014, 6(1):85-93.
Somolinos et al., "Inactivation of *Escherichia coli* by citral," J Appl Microbiol., Jun. 2010 ,108(6):1928-1939.
Somolinos et al., "sigB absence decreased Listeria monocytogenes EGD-e heat resistance but not its Pulsed Electric Fields resistance," Int J Food Microbiol., Jun. 30, 2010, 141(1-2):32-38.
Stevenson et al., "Relationship between cell membrane potential and natural killer cell cytolysis in human hepatocellular carcinoma cells," Cancer Res., Sep. 1, 1989, 49(17):4842-4845.
Tang et al., "Steep pulsed electric fields modulate cell apoptosis through the change of intracellular calcium concentration," Colloids Surf B Biointerfaces., Jun. 15, 2007, 57(2):209-214.
Tarek, "Membrane Electroporation: a molecular dynamics Simulation," Biophys J., 2005, 88:4045-4053.
Traitcheva et al., "Electroporation and alternating current cause membrane permeation of photodynamic cytotoxins yielding necrosis and apoptosis of cancer cells," Bioelectrochemistry., Oct. 2010, 79(2):257-260.
U.S. Food and Drug Administration, "Kinetics of Microbial Inactivation for Alternative Food Processing Technologies—Pulsed Electric Fields", A Report of the Institute of Food Technologists for the Food and Drug Administration of the U.S. Department of Health and Human Services, Mar. 29, 2000, 108 pages.

Veiga et al., "Exposure of human leukemic cells to direct electric current: generation of toxic compounds inducing cell death by different mechanisms," Cell Biochem Biophys., 2005, 42(1):61-74.
Viola et al., "The technology in use for the surgical ablation of atrial fibrillation," InSeminars in Thoracic and Cardiovascular Surgery, Jul. 1, 2002, 14(3):198-205.
Vora et al., "Interstitial implant with interstitial hyperthermia," Cancer, Dec. 1, 1982, 50(11):2518-2523.
Wikipedia.com [online], "Irreversible Electroporation," Sep. 8, 2018, retrieved on Sep. 11, 2019, retrieved from URL <https://en.wikipedia.org/wiki/Irreversible_electroporation>, 13 pages.
Williams et al., "Gene therapy approaches to prolonging corneal allograft survival," Expert Opin Biol Ther., Jul. 2004, 4(7):1059-1071.
Williams, "The Immunotherapy Revolution: The Best New Hope For Saving Cancer Patients' Lives," Gatekeeper Press, Nov. 30, 2019, 115 pages.
Wouters et al., "Membrane permeabilization in relation to inactivation kinetics of *Lactobacillus* species due to pulsed electric fields," Appl Environ Microbiol., Jul. 2001, 67(7):3092-3101.
Yuan et al., "Immunologic responses to xenogeneic tyrosinase DNA vaccine administered by electroporation in patients with malignant melanoma," J Immunother Cancer, Nov. 18, 2013, 1:20.
Zheng et al., "Membrane microfilter device for selective capture, electrolysis and genomic analysis of human circulating tumor cells," J Chromatogr A., Aug. 31, 2007, 1162(2):154-61.
PCT International Preliminary Report on Patentability in International Appln. No. PCT/US2019/066876, dated Jul. 1, 2021, 8 pages.
CA Office Action in Canadian Appln. No. 2,975,123, dated Feb. 8, 2022, 4 pages.
Chen et al., "Intratumoural GM-CSF microspheres and CTLA-4 blockade enhance the antitumour immunity induced by thermal ablation in a subcutaneous murine hepatoma model," International Journal of Hyperthermia, Jan. 1, 2009, 25(5):374-82.
CN Office Action in Chinese Appln. No, 201780012169.0, dated Mar. 14, 2022, 11 pages.
JP Japanese Office Action in Japanese Appln. No. 2018-555838, dated Jan. 20, 2022, 9 pages (with English translation).
CA Office Action in Canadian Appln. No. 2,932,765, dated Jul. 5, 2022, 7 pages.
JP Japanese Office Action in Japanese Appln. No. 2018-555838, dated Nov. 28, 2022, 6 pages (with English translation).

\* cited by examiner

IMMUNOLOGIC TREATMENT OF CANCER

CROSS-REFERENCE TO RELATED APPLICATIONS

This application claims the benefit of U.S. Provisional Application Ser. No. 62/279,579, filed on Jan. 15, 2016. The entire contents of the foregoing are incorporated herein by reference.

TECHNICAL FIELD

This invention relates to methods, compositions, and devices for the immunologic treatment of cancer. More specifically, the present invention relates to the intratumoral administration of immunologic cancer agents and treatments to provide an optimal cancer immune response.

BACKGROUND

Cancer is the second most common cause of death in the US, claiming 580,000 Americans per year, more than 1,500 people each day. The National Institutes of Health (NIH) estimated the overall annual costs of cancer care at more than $227 billion (in 2007); including $89 billion for direct medical costs. Much of the overall healthcare costs of treating cancer are derived from management of the deleterious side effects of radiation and conventional chemotherapy. Immunologic cancer treatment is poised to completely change the landscape of oncologic therapeutics. Checkpoint inhibitors, such as CTLA-4 and PD-1, are already making a major impact in the treatment of metastatic melanoma and non-small cell lung cancer. These drugs are now being used in combination in an attempt to improve their efficacy. The delivery of these drugs is most commonly performed intravenously which can have serious and sometimes fatal systemic toxicities as a result of non-specific distribution of these cytocidal agents in the body, which kill both cancer cells and normal cells and can negatively impact the treatment regimen and patient outcome.

Ablation is a surgical technique used to destroy cells, organs, or abnormal growths (such as cancers). Cryoablation has been known to illicit an immune response in patients through the presentation of a unique array of tumor associated antigens to a patient's antigen presenting cells and dendritic cells. This "cryoimmunologic effect", however, has been known to be variable and in some instances even detrimental. This disclosure provides for a novel method that reduces the toxicities associated with traditional systemic cancer treatments and provides for stimulation of the immune system to the cancer, leading to a tumor targeted immune response.

SUMMARY

The present disclosure is based, at least in part, on the development of new compositions and methods to illicit a cancer immune response through a combination of tumor-directed immunologic cancer treatments and ablation techniques. Intra-tumoral administration of these treatments and procedures may have significant advantages over traditional systemic delivery of anti-cancer drugs. The compositions and methods disclosed herein can allow for smaller than traditional doses to be administered to the subject (e.g., in embodiments wherein the compositions are administered directly into the tumor), a stimulation of the immune system against the tumor antigens, and improved results by placing the drugs in direct proximity to the tumor antigens and the immune inflammatory process.

In one aspect, the present disclosure provides pharmaceutical compositions comprising, consisting essentially of, or consisting of, a combination of at least two immune checkpoint inhibitors and at least one cytokine; each being present in the composition in therapeutically effective amounts, and a pharmaceutically acceptable carrier. The at least two checkpoint inhibitors can comprise inhibitors such as inhibitors of CD137, CD134, PD-1, KIR, LAG-3, PD-L1, CTLA-4, B7.1, B7H3, CCRY, OX-40, and/or CD40. In some embodiments, the composition comprises two checkpoint inhibitors and the two checkpoint inhibitors are a CTLA-4 inhibitor and a PD-1 inhibitor. For example, the CTLA-4 inhibitor can be ipilimumab, tremelimumab or a combination thereof, and the PD-1 inhibitor can be selected from the group consisting of pembrolizumab, nivolumab, pidilizumab, MK-3475, MED 14736 and a combination thereof. In some embodiments, the CTLA-4 inhibitor is ipilimumab and the PD-1 inhibitor is pembrolizumab. In some embodiments, the at least two immune checkpoint inhibitors, and the at least one cytokine are formulated for intra-tumoral administration. A combination of two checkpoint inhibitors and a cytokine produces fewer adverse side effects and/or immune-related adverse events than a combination of the two checkpoint inhibitors (without the cytokine).

The at least one cytokine can be selected from the group consisting of GM-CSF, IL-12, IL-6, IL-4, IL-12, TNF, IFNγ, IFNα, and/or a combination thereof. In some embodiments, the cytokine can be a recombinant granulocyte macrophage colony-stimulating factor (GM-CSF)(e.g., sargramostim). In some embodiments, the compositions can include a first cytokine and a second cytokine. In some instances, the first and the second cytokine are the same and in others they are different.

In some instances, the composition comprises, consists essentially of, or consists of the CTLA-4 inhibitor at a concentration of about 0.5 to 10 mg/ml, the PD-1 inhibitor at a concentration of about 0.5 to 20 mg/ml, and the cytokine at a concentration of approximately 10 to 500 μg/ml. In some instances, the composition comprises the CTLA-4 inhibitor at a concentration of about 1 to 2 mg/ml, the PD-1 inhibitor at a concentration of about 1 to 10 mg/ml and the cytokine at a concentration of about 250 μg/ml. For example, the composition can comprise the CTLA-4 inhibitor at a concentration of about 3.3 mg/ml, the PD-1 inhibitor at a concentration of about 6.6 mg/ml, and the cytokine at a concentration of approximately 16.6 μg/ml. In some instances, the composition is of a volume of at least or approximately 15 ml. In some instances, the composition is of a volume of less than approximately 15 ml. In some instances, the composition comprises about 10 to 300 mg of the CTLA-4 inhibitor, about 10 to 200 mg of the PD-1 inhibitor and about 250 to 500 μg of the cytokine based on a 100 kg subject. For example, the composition can comprise about 50 mg of the CTLA-4 inhibitor, about 100 mg of the PD-1 inhibitor and about 250 μg of the cytokine.

In some instances, the pharmaceutical composition comprises, consists essentially of, or consists of a combination of at least two immune checkpoint inhibitors, and at least one cytokine; each being present in the composition in therapeutically effective amounts, a pharmaceutically acceptable carrier; and a therapeutically effective amount of a nucleic acid drug. The nucleic acid drug can be, e.g. DNA, DNA plasmid, nDNA, mtDNA, gDNA, RNA, siRNA, miRNA, mRNA, piRNA, antisense RNA, snRNA, snoRNA, vRNA, etc. For example, the nucleic acid drug can be a DNA plasmid. In some instances, the DNA plasmid can comprise, consist essentially of, or consist of a nucleotide sequence encoding a gene selected from the group consisting of GM-CSF, IL-12, IL-6, IL-4, IL-12, TNF, IFNγ, IFNα, and/or a combination thereof. The nucleic acid drug can have clinical usefulness, for example, in enhancing the therapeutic effects of the cells or providing a patient with a therapeutic agent. In another instance, the nucleic acid drug may function as a marker or resistance gene. The nucleotide sequence can encode a gene that can be secreted from the cells or cannot be secreted from the cells. The nucleic acid drug can encode a gene and a promoter sequence to increase expression of the gene.

In yet another aspect, the specification provides methods of treating tumor in a patient. For example, the method can comprise, consist essentially of, or consist of administering to the patient intratumorally a composition comprising a combination of at least two immune checkpoint inhibitors and at least one cytokine, each being present in the composition in therapeutically effective amounts, and a pharmaceutically acceptable carrier, in an amount sufficient to treat the tumor. For example, the administered composition may be the compositions described herein. In some instances, the method comprises, consists essentially of, or consists of administering to the patient intratumorally a composition comprising a combination of a CTLA-4 inhibitor, a PD-1 inhibitor, and at least one cytokine, in an amount sufficient to treat the tumor. In some instances, the cytokine is GM-CSF. In some instances, the method further comprises administering a therapeutically effective amount of a nucleic acid drug to the tumor or to the lesion. Administering the combination of two checkpoint inhibitors and a cytokine produces fewer side effects and/or immune-related adverse events than administering the combination of two checkpoint inhibitors (e.g., without a cytokine). The intratumoral administration of the combinations described herein produces fewer side effects and/or immune-related adverse events, when compared to conventional IV administration.

In some instances, administering comprises administering the composition to the patient's tumor using an injection device comprising multiple tines. In some instances, administering comprises administering the composition to the patient's tumor using an injection device comprising a single tine. The composition can be administered in a single dose or can be administered in more than one dose. The compositions can be administered using a probe described herein. The composition can comprise the concentrations described herein. In some embodiments, the composition comprises the CTLA-4 inhibitor at a concentration of approximately 0.5 to 10 mg/ml, the PD-1 inhibitor at a concentration of approximately 0.5 to 20 mg/ml, and the cytokine at a concentration of approximately 10 to 500 µg/ml. In some embodiments, the composition is of a volume of less than approximately 15 ml. In some embodiments, the composition is of a volume of approximately 15 ml. In some embodiments, the at least two immune checkpoint inhibitors, and the at least one cytokine are formulated for intra-tumoral administration.

In some embodiments of the methods described herein, the intratumoral administration of a composition produces fewer adverse side effects and/or immune-related adverse events, when compared to the conventional IV administration of the composition. Adverse side effects and immune-related adverse events of conventional IV administration include gastrointestinal, respiratory, neurologic, endocrine, dermatologic, fatigue, renal, and hepatic effects. In some cases of the methods described herein, the administration of a composition comprising at least two immune checkpoint inhibitors and at least one cytokine produces fewer adverse side effects and/or immune-related adverse events in vivo, when compared to the administration of a composition comprising at least two immune checkpoint inhibitors and no cytokine. In some cases, a composition comprising at least two immune checkpoint inhibitors and at least one cytokine produces fewer adverse side effects and/or immune-related adverse events in vivo, when compared to a composition comprising at least two checkpoint inhibitors without the at least one cytokine. In some instances, the method comprises, consists essentially of, or consists of ablating at least a portion of the tumor thereby creating a zone of lesion. The ablating can be performed, e.g., prior to, concurrently with and/or after administration of the compositions as described herein. The ablating can be performed, e.g., using one or more combinations of ablation methods known in the art, including, for example, cryoablation, thermal ablation, IRE, radiofrequency electrical membrane breakdown (RF-EMB), RF-EMB type ablation, ultrasonic ablation, high-intensity focused ultrasound ablation, ablation using photodynamic therapy, ablation using non-thermal shock waves, cavitation, other mechanical physical cell disruption, or any combination thereof.

In some instances, the methods described herein further comprise ablating at least a portion of the tumor, thereby creating a zone of lesion. In some instances, a first portion or all of a tumor is ablated using a first ablation method and a second portion or all of the tumor is ablated using a second ablation method. The first and the second ablation methods can be different. The first and the second portions of the tumor can be the same or different portions of the tumor. In some instances, the ablating is performed prior to administration of the composition. In some cases, ablating is performed concurrently with administration of the composition or performed after administration of the composition. In some cases, ablating is performed concurrently to and after administration of the composition. In some cases ablating is performed using cryoablation, thermal ablation, IRE, RF-EMB, RF-EMB type ablation, ultrasonic ablation, high-intensity focused ultrasound ablation, ablation using photodynamic therapy, ablation using non-thermal shock waves, cavitation, other mechanical physical cell disruption, or any combination thereof. In some embodiments, ablating of at least a portion is performed using both RF-EMB and cryoablation.

In some instances, the ablating is, at least in part, performed using cryoablation, e.g., using a cryoprobe. The cryoablation can be performed using more than one cryoprobe. The cryoablation can also be performed using any of the probes described herein. In some instances, the ablating is performed using both cyroablation and RF-EMB.

In some instances, the cryoablation step can comprise, consist essentially of, or consist of at least 1 freeze-thaw cycle. For example, the cryoablation can comprise between 1 and 4 freeze-thaw cycles. The freeze portion of the freeze-thaw cycle can be, e.g., at least or about 30 seconds long. The freeze portion of the freeze-thaw cycle can be, e.g., about 30 seconds to 15 minutes long. The freeze portion of the freeze-thaw cycle can be performed, e.g., at a temperature between about −30° C. and −196° C. The thaw portion of the freeze-thaw cycle can be an active thaw process, i.e., with the addition of heat, and/or a passive thaw process, i.e., without the addition of heat.

In some instances, the methods further comprise, consist essentially of, or consist of administering a series of electrical pulses, thereby reversibly electroporating the cells adjacent to the zone of lesion. In some instances, the administration of the electrical pulses is performed concurrently with the ablation. In some instances, the administration of electrical pulses is performed before the ablation. In some instances, the administration of electrical pulses is performed after the ablation. The electrical pulses can be administered via the cryoprobe. In some instances, the series of electrical pulses comprise approximately 1 to 1000 pulses and/or comprise a frequency between 100 and 500 kHz. In some instances, the series of electrical pulses comprise approximately 1 to 4000 pulses and/or comprise a frequency between 100 and 500 kHz. In some instances, the series of electrical pulses comprise approximately 1 to 4000 pulses. In some cases, the series of electrical pulses comprises a frequency between 100 and 500 kHz. The electrical pulses can be, e.g., bipolar and/or have instant charge reversal.

In some instances, the methods further comprise, consist essentially of, or consist of administering a therapeutically effective amount of a nucleic acid drug to the tumor. In some instances, the methods further comprise, consist essentially of, or consist of administering a therapeutically effective amount of a nucleic acid drug to the lesion. The administration of the nucleic acid drug can be performed, e.g., before the administration of electric pulses and/or concurrently with the administration of electric pulses. In some instances, the nucleic acid drug is a therapeutic nucleic acid disclosed herein. In some instances, the nucleic acid drug is a DNA plasmid. For example, the DNA plasmid can comprise a nucleotide sequence encoding a gene selected from the group consisting of GM-CSF, IL-12, IL-6, IL-4, IL-12, TNF, INFγ, IFNα, and/or a combination thereof.

Ablating of at least a portion may be performed using RF-EMB, e.g., using a probe. The probe can be any of the probes disclosed herein. In some instances, the probe administers a series of electrical pulses, thereby creating a zone of lesion immediately adjacent or in relation to the probe and reversibly electroporating the cells adjacent or in relation to the zone of lesion.

In some instances, the series of electrical pulses comprise approximately 1 to 1000 pulses. In some instances, the series of electrical pulses comprises approximately 1 to 4000 pulses. In some instances, the electrical pulses comprise a frequency between 100 and 500 kHz. The electrical pulses can be bipolar. The electrical pulses can also have an instant charge reversal.

In some instances, the methods further comprise administering a therapeutically effective amount of a nucleic acid drug to the tumor. The nucleic acid drug can be any of the therapeutic nucleic acids described herein. In some instances, the nucleic acid drug is a DNA plasmid. For example, the DNA plasmid can comprise a nucleotide sequence encoding a gene selected from the group consisting of GM-CSF, IL-12, IL-6, IL-4, IL-12, TNF, IFNγ, IFNα, and/or a combination thereof.

In some instances of the methods described herein, the portion of the tumor comprises cancer cells, and wherein the ablating is performed under conditions that disrupt cellular membranes of the cells and expose the intracellular components and membrane antigens of the cells.

In some instances, the RF-EMB ablation method creates a unique tissue necrosis characterized by the destruction of cell membrane. Upon destruction of the cellular membrane, the intracellular components and constituent parts of the cell membrane disperse into the extracellular space whereby immunologic identification and response is enhanced. Imaging of a lesion created by RF-EMB ablation on liver tissue shows a unique form of cellular damage with disruption of the cellular membrane and loss of internal organelles such as mitochondria. This is different than other types of ablation methods, such as, for example, IRE, in which the cell membrane remains intact, the cells dies an apoptotic death, and the cell does not expose cellular antigens. In some cases, the degree of cell membrane destruction decreases as distance from the point of ablation increases.

As used herein, the term "RF-EMB type ablation" refers to any ablation technique or combination of techniques which, when performed, yields essentially the same results as RF-EMB ablation. As described herein, RF-EMB ablation and RF-EMB type ablation form lesions having any one or more of the following characteristics: destroyed cellular membranes, non-denatured cellular proteins, non-denatured membrane antigens, enhanced antigen presentation, being capable of co-stimulating the immune system, and the immediate surroundings of the lesion being able to conduct immunologic capable cells and signaling molecules.

In some instances, the portion of the tumor that is ablated comprises cancer cells, and the ablating is performed under conditions that disrupt cellular membranes of the cells and expose the intracellular components and membrane antigens of the cells, e.g., to the body's immune system. The ablation can be performed, e.g., such that intracellular components and membrane antigens of the cells are not denatured by the ablation and/or such that the immediate surroundings of the ablated portion of the tumor are capable of conducting immunologic capable cells and signaling molecules into and out of the ablated tissue. In some instances, the ablation is performed such that the antigens stimulate the immune system. For example, the ablation can be performed, e.g., such that the amount of exposed intracellular components and membrane antigens of the cells is sufficient to stimulate the immune system and/or such that the amount of exposed intracellular components and membrane antigens of the cells do not create immune tolerance.

In some instances, the methods disclosed herein further comprise administering a therapeutically effective amount of a nucleic acid drug to the tumor. The nucleic acid drug can be a therapeutic nucleic acid described herein. In some instances, the nucleic acid drug is a DNA plasmid. In some instances, the DNA plasmid comprises a nucleotide sequence encoding a gene selected from the group consisting of GM-CSF, IL-12, IL-6, IL-4, IL-12, TNF, IFNγ, IFNα, and any combination thereof. In some instances, the methods disclosed herein further comprise reversibly electroporating cells immediately surrounding the ablated portion of the tumor.

In yet another aspect, the present disclosure provides methods of treating a tumor in a patient wherein the method comprises, consists essentially of, or consists of ablating at least a portion of the tumor and administering a therapeutically effective amount of a nucleic acid drug to the tumor. The ablating can be performed, e.g. using RF-EMB, e.g., using a probe. The RF-EMB can comprise administering a series of electrical pulses, thereby creating the zone of lesion immediately adjacent to the probe and reversibly electroporating the cells adjacent to the zone of lesion.

In some instances, the series of electrical pulses comprise approximately 1 to 1000 pulses. In some instances, the series of electrical pulses comprise approximately 1 to 4000 pulses. In some instances, the electrical pulses comprise a frequency between 100 and 500 kHz. In some instances, the electrical pulses are bipolar and/or have instant charge reversal.

In some instances, the nucleic acid drug is a DNA plasmid. The DNA plasmid can comprise nucleotide sequence encoding a gene selected from the group consisting of GM-CSF, IL-12, IL-6, IL-4, IL-12, TNF, IFNγ, IFNα, or any combination thereof.

In some instances, the ablation is performed, e.g., using cryoablation, e.g., using a probe. In some instances, the method further comprises administering a series of electrical pulses, thereby creating a zone of lesion immediately adjacent to the probe and reversibly electroporating the cells adjacent to the zone of lesion. In some instances, the series of electrical pulses comprise approximately 1 to 1000 pulses and/or comprise a frequency between 100 and 500 kHz. In some instances, the series of electrical pulses comprise approximately 1 to 4000 pulses and/or comprise a frequency between 100 and 500 kHz. In some instances, the electrical pulses are bipolar and/or have instant charge reversal. In some instances, the nucleic acid is a DNA and in some instances the DNA plasmid comprises a nucleotide sequence encoding a gene selected from the group consisting of GM-CSF, IL-12, IL-6, IL-4, IL-12, TNF, IFNγ, IFNα, or any combination thereof.

In some instances, the disclosure provides for methods wherein administering the composition comprises administering the composition using an ablation probe that comprises an injection device. In some examples, the ablation probe can further comprise a pump for controlling the speed at which the composition is administered.

In some instances, the disclosure provides for methods wherein the at least one cytokine is a first cytokine, and further comprising administering a therapeutically effect amount of a second cytokine. In some examples, the second cytokine can be the same or different as the first cytokine. The second cytokine can be injected into the tumor. For example, the second cytokine can be injected into the tumor after ablating the tumor. The second cytokine can be administered intravenously, intramuscularly, subcutaneously, and/or a combination thereof.

In some instances, the disclosure provides for methods that further comprise a step of testing the location of the probe prior to administering the composition. The testing of the location of the probe can comprise intratumorally administering a test injection via the probe and measuring the intratumoral pressure during administration of the test injection. In some instances the methods comprise re-locating the probe when increased or decreased intratumoral pressure is detected during the test injection as compared to pressure of the surrounding tumor tissue. For example, increased pressure can be indicative that the probe is within scar tissue and decreased pressure can be indicative that the probe is within a vessel.

In another aspect, the present disclosure provides methods of treating a metastatic cancer in a patient wherein the method comprises, consists essentially of, or consists of administering to the patient intratumorally a composition comprising a combination of at least two immune checkpoint inhibitors, and at least one cytokine, in an amount sufficient to treat the tumor; and ablating at least a portion of the tumor thereby creating a zone of lesion; wherein the ablating is performed under conditions that disrupt cellular membranes of the cells and expose the intracellular components and membrane antigens of the cells such that the antigens stimulate the immune system. In some instances, the ablation is performed such that intracellular components and membrane antigens of the cells are not denatured by the ablation. In some instances, the ablation is performed such that immediate surroundings of the ablated portion of the tumor are capable of conducting immunologic capable cells and signaling molecules into and out of the ablated tissue.

In some instances, the method can further comprise administering a therapeutically effective amount of a nucleic acid drug to the tumor; and administering a series of electrical pulses, thereby electroporating the cells adjacent to the zone of lesion. The nucleic acid drug can be a DNA plasmid. For example, the DNA plasmid can comprise, consist essentially of, or consist of a nucleotide sequence encoding a gene selected from the group consisting of GM-CSF, IL-12, IL-6, IL-4, IL-12, TNF, IFNγ, IFNα, or any combination thereof.

During treatment a skilled practitioner can use a system, e.g., a computer system, computational unit, software and/or algorithm; to plan, target, position, deliver, monitor, adjust, image, and/or test a treatment protocol. A skilled practitioner would understand that RF-EMB involves a number of parameters and variables including, for example, strength of the electric field, frequency, polarity, shape duration, number and spacing, etc.. In some embodiments a skilled practitioner could use an algorithm to control and design the ablation. Any algorithm known in the art can be used in the methods described herein. Examples of computer systems, computational units, software and/or algorithms for use in ablation techniques are known in the art. Ablation techniques and systems are known in the art including for example at least in U.S. Patent Application US20150150618, PCT Application PCT/US14/68774, PCT Application PCT/US2016/015944, PCT Application PCT/US16/16955, PCT Application PCT/US16/16501, PCT Application PCT/US16/16300, and PCT Application PCT/US2016/016352, which are incorporated herein in their entirety.

In another aspect, a probe is provided. In another aspect, a cryoprobe tool is provided. The probe includes, a tool body, a first end which is insertable into a tumor, a second end connectable to a source of gas and to a source of electricity, a cooling head attached to the first end, and at least one electrode attached to the first end, wherein the at least one electrode is configured to ablate a first portion of the tumor and the cooling head is configured to freeze a second portion of the tumor when the first end of the tool is inserted in the tumor. In further aspects, at least one electrode is a wire connected to the source of electricity and to the first end of the probe. At least one electrode is extendable from the tool body. At least one electrode is the body of the probe. The probe also includes at least one needle extendable from the first end of the tool and fluidly connected to a fluid reservoir attached to the second end of the tool. The at least one needle is configured to deliver fluid from the fluid reservoir to the portion of the tumor. The fluid reservoir is plasmids. The at least one needle terminates in multiple tines. The cooling head is extendable from the tool body. The at least one electrode is extendable from the tool body. The probe has thermal insulation covering the body of the tool. The probe has electrical insulation covering the body of the tool. The first portion of the tumor overlaps the second portion of the tumor.

In other aspects, a probe has a central tool body, a first end connected to the central tool body, the first end being insertable into a tumor and having a cooling head, a second end connected to the tool body, the second end connectable to a source of gas, and a sheath configured to enclose a portion of the central tool body. The removable sheath has an electrically insulated body, connectors configured to attach to an electrical source, and electrical contacts configured to connect with an electrically conductive portion of the central tool body, wherein the removable sheath is configured to ablate a first portion of the tumor by transmitting electrical impulses from the electrical source along the central tool body and to the first end, and wherein the cooling head is configured to freeze a second portion of the tumor when the first end of the tool is inserted in the tumor.

In further aspects, the sheath is removable from the central tool body. The probe is attachable to an indifferent electrode.

Further embodiments include a system for the administration of cryotherapy in combination with electric pulses, the system including a tool including a tool body, a first end which is insertable into a tumor and a second end, a cooling head attached to the first end, and at least one electrode attached to the first end, wherein the at least one electrode is configured to ablate a first portion of the tumor and the cooling head is configured to freeze a second portion of the tumor when the first end of the tool is inserted in the tumor, a cryomachine for supplying the gas to the tool via the second end of the tool, and an electric pulse generator for supplying electric pulses to the tool via the second end of the tool.

In still further aspects, the system has a second tool that has a second tool body, a first end of the second tool which is insertable into a tumor, a second end of the second tool connectable to the cryomachine and electric pulse generator, a cooling head attached to the first end of the second tool and a second electrode attached to the first end of the second tool. In the system the second electrode and the at least one electrode are configured to ablate the first portion of the tumor which extends between the second electrode and the at least one electrode, and the cooling head of the second tool is configured to freeze a third portion of the tumor when the first end of the tool and the first end of the second tool are inserted in the tumor. The system can have a second tool, the second tool having a tool body, a first end which is insertable into a tumor, a second end connectable to a source of electricity, a second electrode attached to the first end, wherein the first portion of the tumor extends between the at least one electrode and the second electrode. The system can have an indifferent electrode electrically connected to the source of electricity.

As used herein, the term "nucleic acid drug" or "therapeutic nucleic acid" refers to a nucleotide, nucleoside, oligonucleotide or polynucleotide that is used to achieve a desired therapeutic effect. Exemplary nucleic acid drugs include, e.g., DNA, nDNA, mtDNA, gDNA, RNA, siRNA, miRNA, mRNA, piRNA, antisense RNA, snRNA, snoRNA, vRNA, etc. For example, the nucleic acid drug can be a DNA plasmid.

The term "subject" is used throughout the specification to describe an animal, human or non-human, to whom treatment according to the methods of the present invention is provided. Veterinary applications are clearly anticipated by the present invention. The term includes but is not limited to birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs. The term "treat(ment)," is used herein to denote delaying the onset of, inhibiting, alleviating the effects of, or prolonging the life of a patient suffering from, a condition, e.g., cancer.

An "effective amount" is an amount sufficient to effect beneficial or desired results. For example, a therapeutically effective amount is one that achieves the desired therapeutic effect. Effective amounts of compositions described herein for use in the present invention include, for example, amounts that enhance the immune response against tumors and/or tumor cells, improve the outcome for a patient suffering from or at risk for cancer, and improve the outcome of other cancer treatments. An effective amount can be administered in one or more administrations, applications or dosages. A therapeutically effective amount of a pharmaceutical composition (i.e., an effective dosage) depends on the pharmaceutical composition selected. A therapeutically effective amount of a pharmaceutical composition depends on the method of administration selected. In some cases, intra-tumoral administration of a composition reduces the therapeutically effective amount of a composition, when compared to intravenous administration (e.g., conventional IV administration). The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

The details of one or more embodiments of the invention are set forth in the accompanying drawings and the description below. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features, objects, and advantages of the invention will be apparent from the description and drawings, and from the claims.

DESCRIPTION OF DRAWINGS

FIG. 1A is a CT scan of Patient A's pelvic region before treatment. FIG. 1B is a CT scan of Patient A's pelvic region after treatment.

FIG. 3A is a CT scan of Patient B's pelvic region before treatment. FIG. 3B is a CT scan of Patient B's pelvic region after treatment.

Like reference symbols in the various drawings indicate like elements.

DETAILED DESCRIPTION OF THE INVENTION

Figures 1A, 1B:
FIGS. 1A-B are images of CT scans of Patient A's pelvic region before and after treatment with a CTLA-4 inhibitor, a PD-1 inhibitor, and a cytokine in addition to an RF-EMB type ablation. Arrows point to locations of the initial tumor structures before treatment (FIG. 1A) and after treatment (FIG. 1B).

The present disclosure is based, at least in part, on new compositions for cancer treatment that include at least two immune checkpoint inhibitors and at least one cytokine, each being present in the combination in therapeutically effective amounts and in a pharmaceutically acceptable carrier. This combination can in some instances further comprise a nucleic acid drug. The present disclosure is also based, at least in part, on the development of a new method for the treatment of cancer that comprises administering to a patient intra-tumorally a composition as disclosed herein. Further described are devices configured for performing certain methods described herein.

The compositions, methods, and devices described herein are particularly useful for treating cancer in subjects. The term "cancer" refers to cells having the capacity for autonomous growth. Examples of such cells include cells having an abnormal state or condition characterized by rapidly proliferating cell growth. The term is meant to include cancerous growths, e.g., tumors; metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus.

The compositions, methods, and devices described herein can be used to treat naturally arising cancer in a subject. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections.

Treatment of carcinomas, adenocarcinomas, and sarcomas is within the present invention. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Cancers that may be treated using the methods, compositions, and devices of the present invention include, for example, cancers, e.g., tumors, of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and throat; sarcomas, choriocarcinomas, and lymphomas, among others.

Metastatic tumors can be treated using methods described herein. For example, performing a treatment method described herein on a tumor located at one site in the subject's body (e.g., a primary tumor), can stimulate the subject's immune defenses against the tumor and cause an immune attack on tumors of the same or even different type of at another site(s) in the subject's body (e.g., a metastatic tumor). A metastatic tumor can arise from a multitude of primary tumor types, including but not limited to those of prostate, colon, lung, breast, bone, and liver origin. Metastases develop, e.g., when tumor cells shed from a primary tumor adhere to vascular endothelium, penetrate into surrounding tissues, and grow to form independent tumors at sites separate from a primary tumor.

Skilled practitioners will appreciate that the compositions, methods and devices described herein can also be used to treat non-cancerous growths, e.g., non-cancerous tumors. Exemplary non-cancerous growths include, e.g., benign tumors, adenomas, adenomyoepthelioma, ductal or lobular hyperplasia, fibroadenomas, fibromas, fibrosis and simple cysts, adenosis tumor, hematomas, hamartomas, intraductal papillomas, papillomas, granular cell tumors, hemangiomas, lipomas, meningiomas, myomas, nevi, osteochondromas, phyllodes tumors, neuromas (e.g., acoustic neuromas, neurofibromas, and pyogenic granulomas), or warts (e.g., plantar warts, genital warts, flat warts, periungual warts, and filiform warts).

Skilled practitioners will appreciate that a subject can be diagnosed by a physician (or veterinarian, as appropriate for the subject being diagnosed) as suffering from or at risk for a condition described herein, e.g., cancer, by any method known in the art, e.g., by assessing a patient's medical history, performing diagnostic tests, and/or by employing imaging techniques.

As described herein, one exemplary method of treating a tumor in a patient comprises the steps of: (i) optionally, prior to performance of the method, identifying the location of the tumor within the patient; (ii) intratumorally administering a pharmaceutical composition described herein to the tumor (e.g., a pharmaceutical composition comprising at least two immune checkpoint inhibitors and at least one cytokine); (iii) optionally ablating at least a portion of the tumor; (iv) optionally administering a therapeutically effective amount of a nucleic acid drug to the tumor; and (v) optionally administering a series of electric pulses to the tumor such that the area around the lesion is reversibly electroporated. Identifying a location of the tumor can be performed by techniques known in the art (e.g., X-ray radiography, magnetic resonance imaging, medical ultrasonography or ultrasound, endoscopy, elastography, tactile imaging, thermography, medical photograph, nuclear medicine imaging techniques including positron emission tomography and single-photon emission computed tomography, photoacoustic imaging, thermography, tomography including computer-assisted tomography, echocardiography and functional near-infrared spectroscopy, etc.). The optional step of ablating the tumor (iii) can occur before, concurrently, or after administering a pharmaceutical composition (ii), and the ablation can create an area of lesion exposing intracellular components and membrane antigens of the tumor. Ablation can be performed using a technique described herein on a portion or all of the tumor. Optionally administering a therapeutically effective amount of a nucleic acid drug to the tumor (iv) can occur before, concurrently or after the of steps (ii) and (iii). Optionally administering a series of electric pulses to the tumor (v) can occur concurrently or after the administration of the nucleic acid drug (iv); or before, concurrently and/or after steps (ii) and (iii).

Accordingly, provided herein are pharmaceutical compositions comprising the mixture of checkpoint inhibitors and cytokine(s). Check point inhibitors work to activate the immune system to attack tumors, inhibiting the immune response proteins responsible for down regulating the immune system. The check point inhibitors can be, e.g., inhibitors of CD137, CD134, PD-1, KIR, LAG-3, PD-L1, CTLA-4, B7.1, B7H3, CCRY, OX-40, and/or CD40. The pharmaceutical compositions can comprise any combination of check point inhibitors. For example, particularly useful in is a combination of a PD-1 inhibitor and a CTLA-4 inhibitor. A skilled practitioner would appreciate that many other combination are also useful. A non-limiting list of combinations include a CD137 inhibitor and a CD134 inhibitor; a PD-1 inhibitor and a MR inhibitor; a LAD-3 inhibitor and a PD-L1 inhibitor; a CTLA-4 inhibitor and a CD40 inhibitor; a CD134 inhibitor and a PD-1 inhibitor; a MR inhibitor and a LAG-3 inhibitor; a PD-L1 inhibitor and a CTLA-4 inhibitor; a CD40 inhibitor and a CD137 inhibitor; a CTLA-4 inhibitor and a PD-L1 inhibitor; a PD-1 inhibitor and a CD40 inhibitor, or any combination of two or more checkpoint inhibitors known in the art. The pharmaceutical compositions can also comprise at least cytokine. The at least one cytokine can comprise GM-CSF, IL-12, IL-6, IL-4, IL-12, TNF, IFNγ, IFNα, and/or a combination thereof. The compositions can include a first cytokine and a second cytokine. A skilled practitioner would appreciate that in some instances the first and the second cytokine can be different.

Traditionally, checkpoint inhibitors are administered intravenously, which can result in serious and sometimes fatal systemic toxicities as a result of non-specific distribution of these cytocidal agents in the body. The non-specific distribution of these agents kills both cancer cells and normal cells and can negatively impact the treatment regimen and patient outcome. The present intra-tumoral methods can reduce systemic toxicity and produce fewer side effects by sequestering the drugs in the tumor microenvironment and sparing normal cells and tissues from the toxicity of the drugs (Intratumoral Immunization: A New Paradigm for Cancer Therapy. Clin Cancer Res. 2014 April 1; 20(7): 1747-1756. doi:10.1158/1078-0432.CCR-139-2116). The present intra-tumoral methods can reduce systemic toxicity and product fewer side effects by also lowering the amount of the administered compositions necessary to be therapeutically effective. Moreover, by combining techniques that target both the cancer cells and the immune system, the pharmaceutical composition can be more effective at not only inhibiting the cancer but also triggering an effective antitumor immune response. This antitumor immune response may then target metastatic sites and eliminate cancer throughout the subject.

The compositions can further include one or more therapeutic and/or biologic agents known in the art to be effective in treating cancer, i.e., an anti-cancer agent, or known in the art to be effective in stimulating the immune system, i.e., immunostimulant or immunomodulator. Such pharmaceutical compositions can be used to treat cancer as described above.

In some instances, the pharmaceutical composition further comprises a therapeutically effective amount of a nucleic acid drug. The nucleic acid drug can be, e.g. DNA, nDNA, mtDNA, gDNA, RNA, siRNA, miRNA, mRNA, piRNA, antisense RNA, snRNA, snoRNA, vRNA, etc. For example, the nucleic acid drug can be a DNA plasmid. Such a DNA plasmid can comprise, consist essentially of, or consist of a nucleotide sequence encoding a gene selected from the group consisting of GM-CSF, IL-12, IL-6, IL-4, IL-12, TNF, IFNγ, IFNα, and/or a combination thereof. The nucleic acid drug can have clinical usefulness, for example, enhancing the therapeutic effects of the cells or providing a patient with a therapeutic agent. In other instances, the nucleic acid drug may function as a marker or resistance gene. The nucleotide sequence can encode a gene that can be secreted from the cells or cannot be secreted from the cells. The nucleic acid drug can encode a gene and a promoter sequence to increase expression of the gene.

One of skill in the art would appreciate that the presently described compositions can be adapted according to the individual aspects of the cancer and/or the subject, e.g., size of the tumor, location of the tumor, subject, clinical evidence of drug response, etc.

A pharmaceutical composition provided herein can include a delivery agent or pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into pharmaceutical formulations that contain an antibody or antigen-binding fragment thereof as described herein.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

The pharmaceutical compositions described herein (e.g., the checkpoint inhibitors, cytokines, nucleic acid drugs, and/or a combination thereof) may be intra-tumorally delivered via an injection device, wherein the injection device may be part of a probe. The probes as described herein can be configured for the various ablation methods. Further, the probe can also be configured to combine the methods described herein, e.g., a cryoprobe can be configured to administer an electric pulse, a cryogen and/or a composition of drugs.

Pharmaceutical compositions suitable for injection can include sterile aqueous solutions (where water soluble), dispersions, and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiments, the therapeutic compounds can be prepared with carriers that will protect the therapeutic compounds against rapid elimination from the body, such as a controlled release formulation, including implants and microencapsulated delivery systems.

The pharmaceutical compositions can be included in a container, pack, cartridge, or dispenser together with instructions for administration.

The therapeutic and/or biologic agents can be administered in an effective amount, at dosages and for periods of time necessary to achieve the desired result. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

In some embodiments of the methods described herein, the compositions described herein can be administered in one or more administrations. These one or more administrations can be of the same or different methods of administration, including, for example, intravenously, intramuscularly, subcutaneously, intra-tumorally or any combination thereof. In some cases, for example, a first composition is administered intra-tumorally and a second composition is administered subcutaneously. In some cases, first and the second compositions are administered simultaneously, in sequence, or in a series of treatments. In some cases, first and the second compositions are the same, different, or the same in part. In some cases, the methods described herein include two or more administrations. In some cases a first administration is an intra-tumoral administration of at least two checkpoint inhibitors (e.g., a PD-1 inhibitor and a CTLA-4 inhibitor) and at least one cytokine (e.g., GM-CSF).

Dosage regimens can be adjusted to provide the optimum therapeutic response. For example, several divided doses can be administered daily or the dose can be proportionally reduced as indicated by the exigencies of the therapeutic situation. Those skilled in the art will be aware of dosages and dosing regimens suitable for administration of the new monoclonal antibodies disclosed herein or antigen-binding fragments thereof to a subject. See e.g., Physicians' Desk Reference, 63rd edition, Thomson Reuters, Nov. 30, 2008. For example, Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Methods of treating cancer disclosed herein optionally employ ablation of at least a portion of a tumor. One of the unique aspects of ablation, versus surgical removal, is that the tumor is left in situ for the body's defense and healing mechanisms to remove it. This creates an opportunity to harness the body's immune defense mechanisms to recognize the dead tumor and essentially auto-immunize the patient to their own cancer. Moreover, by stimulating the immune system to the cancer cell antigens, the methods disclosed herein can (i) treat primary tumors; (ii) activate the immune response to cancer cell antigens; and (iii) induce immune system targeting of metastatic lesions.

As described herein, the method of ablation influences at least two factors that are known to influence the immunologic response to an ablated tumor. One is the effect of the ablation process on the protein structure and therefore the antigenicity of the tumor proteins. The second factor is the mechanism of cell death related to the ablation modality. Necrosis, under certain conditions, ruptures the cell and spills a wide range of intracellular contents into the extracellular environment that causes co-stimulation of dendritic cells, leading to T Cell proliferation and activation. Apoptosis, which leaves the cells intact, confines the cellular contents and prevents co-stimulation. This lack of intracellular exposure and co-stimulation mutes the immunologic effect by preventing T cell activation and proliferation.

There are many processes of ablation known in the art, including cryoablation, thermal ablation, IRE, RF-EMB, RF-EMB type ablation, ultrasonic ablation, high-intensity focused ultrasound ablation, ablation using photodynamic therapy, ablation using non-thermal shock waves, cavitation, other mechanical physical cell disruption, or any combination thereof. These different types of ablation methods can have different outcomes on the protein structures and mechanism of cell death. For example, heat ablation destroys structures due to denaturing proteins and it also destroys the underlying collagen matrix of the tissue. This disruption of the proteins and tissue makes a robust immunologic response unlikely. Cold, e.g. cryoablation, can denature proteins and can disrupt both protein and tissue structure. Irreversible electroporation (IRE) and non-thermal ablation modalities, e.g., RF-EMB, etc., are structure sparing and can therefore be used to treat cancers in the pancreas, central liver, and other areas such as the head and neck. IRE is a technique where an electrical field is applied to cells in order to increase the permeability of the cell membrane. The high voltage of IRE destroys the target cells while leaving neighboring cells unaffected. IRE, however, causes apoptotic cell death, and as described above, this is not optimal for an immunologic reaction. Radiofrequency electrical membrane breakdown RF-EMB) is another non-thermal modality that produces necrosis by complete breakdown of the cell membrane electrically (see, Onik PCT/US2014/068774, which is incorporated herein in its entirety). Under certain conditions, RF-EMB can also be used to deliver DNA plasmids. Reversible electroporation (RE) can also be used to deliver DNA plasmids. RE is similar to IRE, however the electricity applied to the target cells is below the electric field threshold of the target cells. Therefore, the cells can recover when the electric field is removed and rebuild their cellular membranes and continue with cellular functions. RE can be used as a tool for gene therapy as the reversible element allows for entry of nucleic acids (e.g. DNA plasmids) into a viable cell.

An ablation method described herein can be used alone or in combination with other ablation methods. Two or more ablation methods can be used in combination. The methods may be applied sequentially or concurrently. In some cases, a combination of ablation methods has a synergistic effect on the tissue. A non-limiting list of combinations includes, for example, heat ablation and RF-EMB, cryoablation and RF-EMB, IRE and RF-EMB, RE and RF-EMB, IRE and cryoablation, heat ablation and cryoablation, heat ablation and IRE, RE and IRE, heat ablation with RE, and any combination in which two or more methods are used. The two or more ablation methods can be used concurrently or sequentially.

In some cases, methods described herein create an RF-EMB type lesion using a combination of RF-EMB and cryoablation techniques. This combination of ablation methods can produce a synergistic effect on the tissue. The synergistic effect can be the creation of an RF-EMB type lesion with less required energy input than with other means. The result, for instance in liver tissue includes: in areas adjacent to aseptic non-inflammatory coagulative necrosis, there is alteration of liver architecture, including dilation of bile duct canaliculi, as well as unique diffuse alteration of cytoplasmic organelles, including distortion of mitochondrial cristae and vacuolization of endoplasmic reticulum.

One of skill in the art would appreciate that the administration of compositions or treatments, as disclosed in the methods herein, can be adapted according to the individual aspects of the cancer, e.g., size of the tumor, location of the tumor, the subject. One of skill in the art would appreciate the variables of each of the various methods of ablation are known and described in the art (including, for example, *Percutaneous Prostate Cryoablation.* Edited by Gary Onik, Boris Rubinsky, Graham Watson, and Richard Ablin. Quality Medical Publishing, St Louis, Mo. 1995 which is incorporated herein in its entirety).

As examples of the variability and variety of ablation parameters, as described herein, the process of cryoablation includes variables that can be adjusted, e.g. the number of freeze-thaw cycles, the speed of the freeze, the thaw portion of the cycle, etc, to influence the outcome of the ablation, e.g., the size of the lesion, damage to surrounding tissue, and the immune response to the lesion. Similarly, the process of RF-EMB, includes variables such as strength of the electric field, frequency, polarity, shape duration, number and spacing, etc., which can similarly influence the outcome of the ablation. The proximity of a tumor cell to the electric pulse will determine the strength and outcome of the RF-EMB on any particular cell. For example, as the electric field strength diminishes from the point of administration (e.g., the probe), the cells furthest from the point of administration are treated with a lower strength electric field and as such may not be ablated but rather reversibly electroporated.

Additionally the use of reversible electroporation (RE) for the delivery of gene therapy can be modified to determine the range, reversibility and delivery of the electroporation around the lesion. One of skill in the art would appreciate the variables of electroporation are known and described in the art (Kee Stephen T, Gehl Julie, Lee Edward W. Clinical aspects of electroporation. New York: Springer; 2011. ISBN 978-1-4419-8362-6 # 256 pages, which is incorporated herein in its entirety). These variables include but are not limited to varying the strength of the electric pulse, timing of electric pulse, number of pulses, the polarity of the pulse, etc,. As described herein, the ablating of the tumor can occur at the same time, before or after the administration of the pharmaceutical mixture. The nucleic acid drug can be administered before, after or during the process of ablation. The nucleic acid drug can be administered before, after or during the administration of the pharmaceutical mixture. The nucleic acid drug can also be administered before or during the process of electroporation.

The methods can be used alone or in combination with other methods for treating cancer in patients. Accordingly, in some instances, the methods described herein can further include treating the patient using surgery (e.g., to remove a portion of the tumor), chemotherapy, immunotherapy, gene therapy, and/or radiation therapy. Compositions and methods described herein can be administered to a patient at any point, e.g., before, during, and/or after the surgery, chemotherapy, immunotherapy, gene therapy, and/or radiation therapy.

Also provided are kits that include one or more of the pharmaceutical compositions described herein. Kits generally include the following major elements: packaging, reagents comprising binding compositions as described above, optionally a control, and instructions. Packaging can be a box-like structure for holding a vial (or number of vials) containing said binding compositions, a vial (or number of vials) containing a control, and/or instructions for use in a method described herein. In some cases the packaging contains a cartridge that can be controlled by a digital device following systematic instructions. Individuals skilled in the art can readily modify the packaging to suit individual needs.

In some embodiments, a kit provided herein can include at least one (e.g., one, two, three, four, five, or more) composition containing at least one (e.g., one, two, three, four, five, or more) of the compositions described herein, and at least one (e.g., one, two, three, four, five, or more) other composition in a separate vial containing a therapeutic or biologic agent known in the art to be effective in treating cancer.

Compositions and kits as provided herein can be used in accordance with any of the methods (e.g., treatment methods) described above. For example, compositions and kits can be used to treat cancer. Those skilled in the art will be aware of other suitable uses for compositions and kits provided herein, and will be able to employ the compositions and kits for such uses.

Devices

In some embodiments, an injection device is a cryoprobe that can emit electric pulses and also deliver plasmids.

Figure 5:
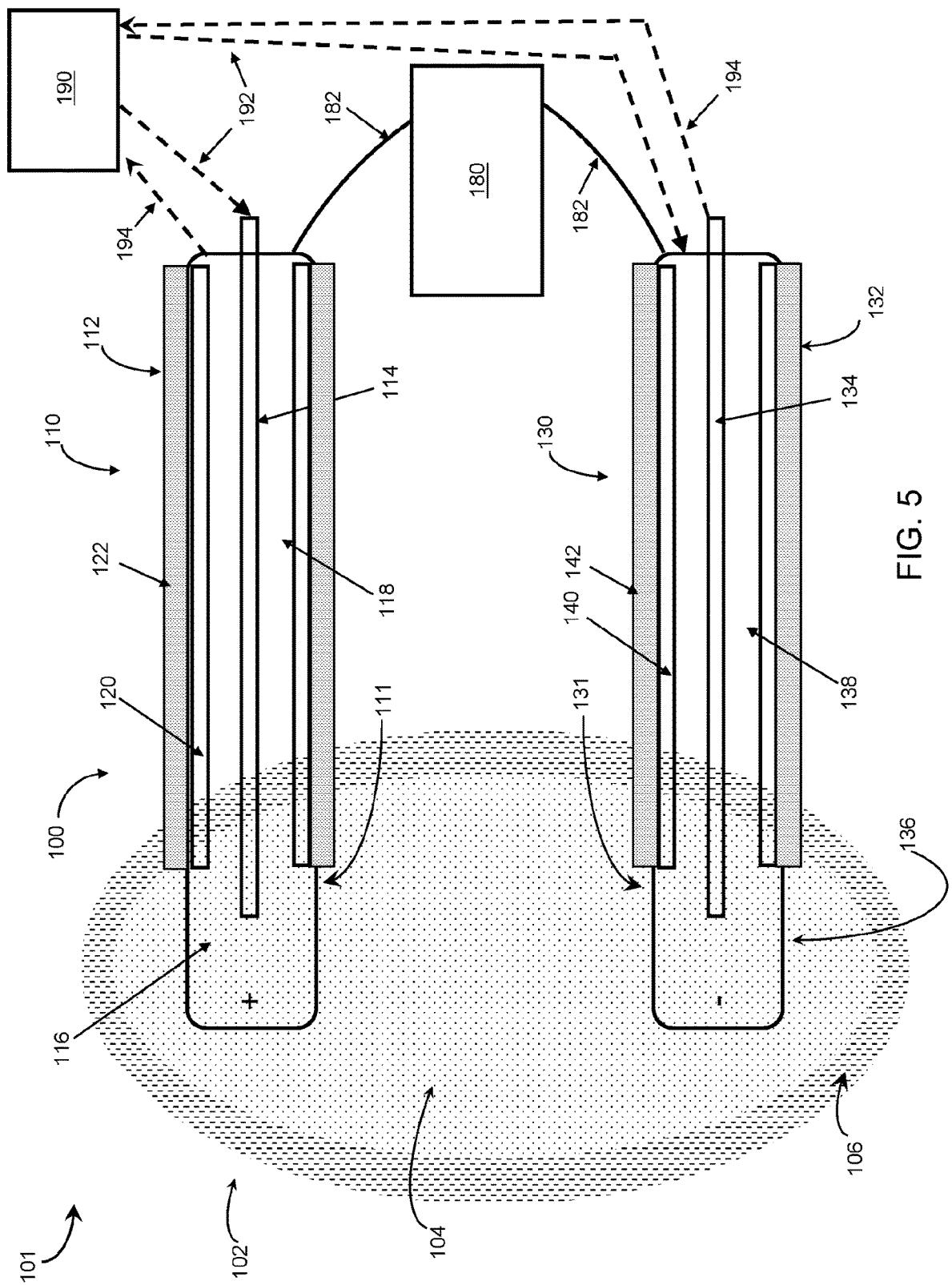
FIG. 5 is a device having two cryoprobe electrodes and the ability to deliver electrical pulses and create reversible electroporation.

Referring to FIG. 5, an injection device 100 is part of a system 101 that is capable of administering both extreme cold as well as electric pulses to tissues and/or tumors. The injection device 100 has two electrode cryoprobes, including a positively-charged cryoprobe 110 and a negatively-charged cryoprobe 130. Each cryoprobe 110, 130 is a generally cylindrical probe that is inserted into a target tissue 102 ata first end 111, 131 and grasped by a user ata second end 112, 132. Each cryoprobe 110, 130 can be individually manipulated by a user. Alternatively, both cryoprobes 110, 130 can be contained within a larger housing (not shown for clarity) that permits the user to insert both cryoprobes 110, 130 into the target tissue 102 simultaneously at a known distance from each other. In some embodiments, the two cryoprobes 110, 130 contained within a housing can be arranged such that the distance separating the two cryoprobe electrodes 110, 130 can be increased or decreased by the user.

Each cryoprobe 110, 130 has a central gas supply cannula 114, 134 running from the first ends 111, 131 to the second ends 112, 132 of the cryoprobes 110, 130. Each central gas supply cannula 114, 134 is attached at the second end 112, 132 of each probe to a cryomachine 190. The cryomachine 190 serves as a source of cooled gas that is pumped via gas supply lines 192 to enter the central gas supply cannulas 114, 134 at the second ends 112, 132 of the cryoprobes and be delivered to cooling heads 116, 136 at the first ends 111, 131 of the cryoprobes and thereby to the tissue 102. The cooling heads 116, 136 are configured to pierce and be inserted into the tissue 102 as is known in the art, and can be flat or pointed in shape. The cooling heads 116, 136 are generally made of metal or other material that has a high conductance so as to allow the cold gas entering the cooling heads 116, 136 via the central gas supply cannulas 114, 134 to thermally interact with the tissue 102.

Gas return channels 118, 138 concentrically surround the central gas supply cannulas 114, 134 and are fluidly connected to the cannulas such that cooled gas enters the cooling heads 116, 136 and then flows back through the gas return channels 118, 138 to return to the cryomachine 190 via gas return lines 194. Layers of thermal insulation 120, 140 protect the user grasping the cryoprobes 110, 130 from the cold gas running through the gas return channels 118, 138. Layers of electrical insulation 122, 142 and the layers of thermal insulation 120, 140 concentrically surround the outer surfaces of the gas return channels 118, 138 . The layers of electrical insulation 122, 142 protect the user and electrically isolate the body of each cryoprobe 110, 130 from electrical pulses generated by an electrical pulse generator 180. The order of layers of electrical insulation 122, 142, thermal insulation 120, 140 and the outer surfaces of the gas return channels 118, 138 may be placed in differing orders.

The electrical pulse generator 180 is connected by wires 182 to the second ends 112, 132 of the cryoprobes 110, 130 such that electrical pulses are transmitted to the cooling heads 116, 136 and in turn administered to the tissue 102. The cooling heads 116, 136 therefore serve the dual function of administering cold as well as the electrical impulses to the target tissue 102. The electrical pulses can be transmitted along the length of the cryoprobes 110, 130 via wires layered between the layers of electrical insulation 122, 142 and the layers of thermal insulation 120, 140. In some embodiments, at least a portion of the gas return channels 118, 138 are electrically conductive and also serve the function of transmitting the electrical pulses to the tissue 102 via the cooling heads 116, 136.

The electrical pulse generator 180 is arranged to generate a positive charge via the positively-charged cryoprobe 110 and a negative charge via the negatively-charged cryoprobe 130. The injection device 100 is therefore capable of delivering electrical pulses as well as cold temperatures to the target tissue 102. For simplicity, the positively-charged cryoprobe 110 and the negatively-charged cryoprobe 130 can be identical in structure.

The two cryoprobes 110, 130 are inserted into the target tissue 102 at a desired distance of separation from each other (e.g., 2 mm, 5 mm, 10 mm), thereby creating a cryolesion zone 104 that surrounds and extends between the tips of the cryoprobes 110, 130. This arrangement of the two cryoprobes 110, 130 also creates an RE (Reversible Electroporation) zone 106 in relation to the cryolesion zone 104.

The configuration of the cryolesion zone 104 can be varied by the user. In some instances, the cooling heads 116, 136 are retractable into the bodies of the cryoprobes 110, 130, e.g., the length of the cooling heads 116, 136 extending from the end of the thermal insulation layers 120, 140 can be reduced by retracting the cooling heads 116, 136 such that more or all of their surface area is covered by the thermal insulation layers 120, 140. Similarly, the length of the cooling heads 116, 136 extending from the end of the thermal insulation layers 120, 140 can be increased by extending the cooling heads 116, 136 such that less of their surface area is covered by the thermal insulation layers 120, 140. The insulation layers 120, 140 and 122, 144 are repositionable during use of the injection device 100. The user can also modify the temperature of the gas exiting the cryomachine 190 and entering the tissue 102. The configuration of the RE zone 106 can be varied by the user by modulating the electrical pulses exiting the electrical pulse generator 180. The variables can be altered such that the cryolesion zone 104 is smaller than, the same size as, or larger than the RE zone 106.

Figure 6:
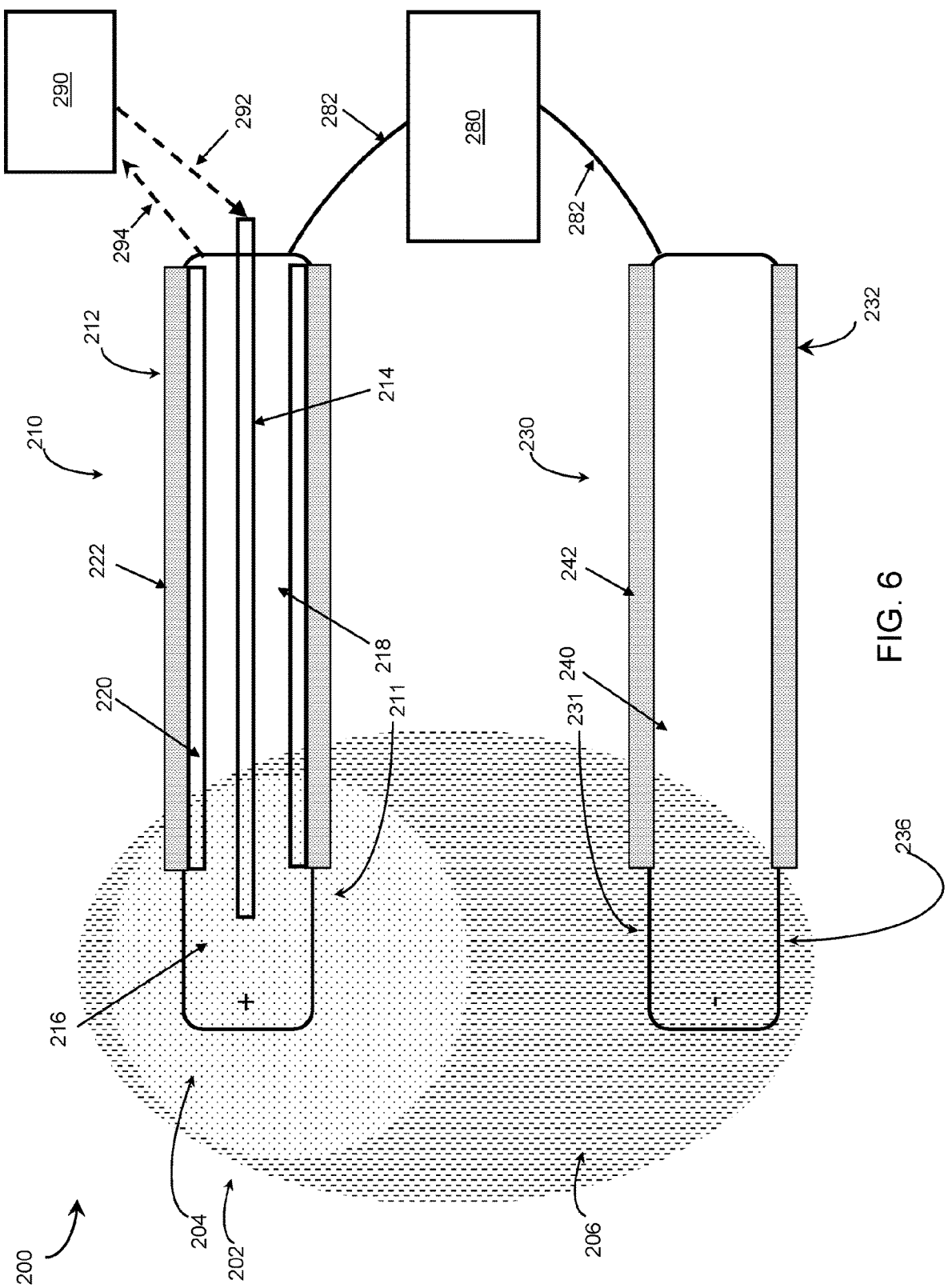
FIG. 6 is an embodiment of a device having one cryoprobe electrode and one non-cryoprobe electrode.

Referring to FIG. 6, an additional embodiment of an injection device 200 that is capable of delivering both cold and electrical pulses to a target tissue 202 is shown. Many of the elements of the electrode cryoprobe 200 are identical to those shown in FIG. 5. A positively-charged cryoprobe 210 has a first end 211 and a second end 212, and a central gas supply cannula 214 running from the first end 211 to the second end 212. The central gas supply cannula 214 is attached at the second end 212 to a cryomachine 290 that is a source of cooled gas that is pumped via a gas supply line 292 to enter the central gas supply cannula 214 and be delivered to a cooling head 216 at the first end 211 of the cryoprobe and thus to the tissue 202. The cooling head 216 is configured to pierce and be inserted into the tissue 202 as is known in the art, and can be flat or pointed in shape, and is generally made of metal or other material that has a high conductance.

A gas return channel 218 concentrically surrounds the central gas supply cannula 214 and is fluidly connected to the cannula 214 such that cooled gas enters the cooling head 216 and then flows back through the gas return channel 218 to return to the cryomachine 290 via a gas return line 294. A layer of thermal insulation 220 protects the user grasping the cryoprobe 210 from the cold gas running through the gas return channel 218. A layer of electrical insulation 222 concentrically layers the outer surface of the gas return channel 218 which also concentrically surrounded by the layer of thermal insulation 220.

An electrical pulse generator 280 is connected by wires 282 to the second end 212 of the cryoprobe 210 and also to the second end 232 of an electric probe 230. The electric probe 230 is similar to cryoprobe 210, having a first end 231 that is insertable into the tissue 202 and a second end 232 that connects to the electrical pulse generator 280. However the electric probe 230 is not connected to the cryomachine 290 and does not have the structure (e.g., a central gas supply cannula, a gas return channel, gas supply and return lines) to administer cryotherapy to the tissue 202. The electric probe 230 has a tissue insertion head 236 that does not cool the tissue 202 but does administer the electric therapy. The electric pulse generator 280 transmits electrical pulses to the cooling head 216 and tissue insertion head 236 and in turn to the tissue 202. The cooling head 216 therefore serves the dual function of administering cold as well as the electrical impulses to the target tissue 202 while the tissue insertion head 236 administers the electrical impulses only. The electrical pulses can be transmitted along the length of the cryoprobe 210 and electric probe 230 via wires attached to layers of electrical insulation 222, 242. In some embodiments, at least a portion of the bodies of the cryoprobe 210 and electric probe 230 are electrically conductive and also serve the function of transmitting the electrical pulses to the tissue 202. The electrical pulse generator 280 is arranged to generate a positive charge via the positively-charged cryoprobe 210 and a negative charge via the negatively-charged electric probe 230.

The cryoprobe 210 and electric probe 230 are inserted into the target tissue 202 at a desired distance of separation from each other (e.g., 2 mm, 5 mm, 10 mm), thereby creating an RE zone 206 that surrounds and extends between the cryoprobe 210 and electric probe 230. As only cryoprobe 210 administers cold to the tissue 202, a created cryolesion zone 204 is smaller than the cryolesion zone 104 created with two cryoprobes and surrounds the first end 211 of the cryoprobe 210.

The configuration of the cryolesion zone 204 can be varied by the user as for cryoprobe injection device 200 by arranging the cooling head 216 to be retractable into the body of the cryoprobes 210. The user can also modify the temperature of the gas exiting the cryomachine and entering the tissue 202. The size of the RE zone 206 can be varied by modulating the electrical pulses exiting the electrical pulse generator 180.

Figure 7:
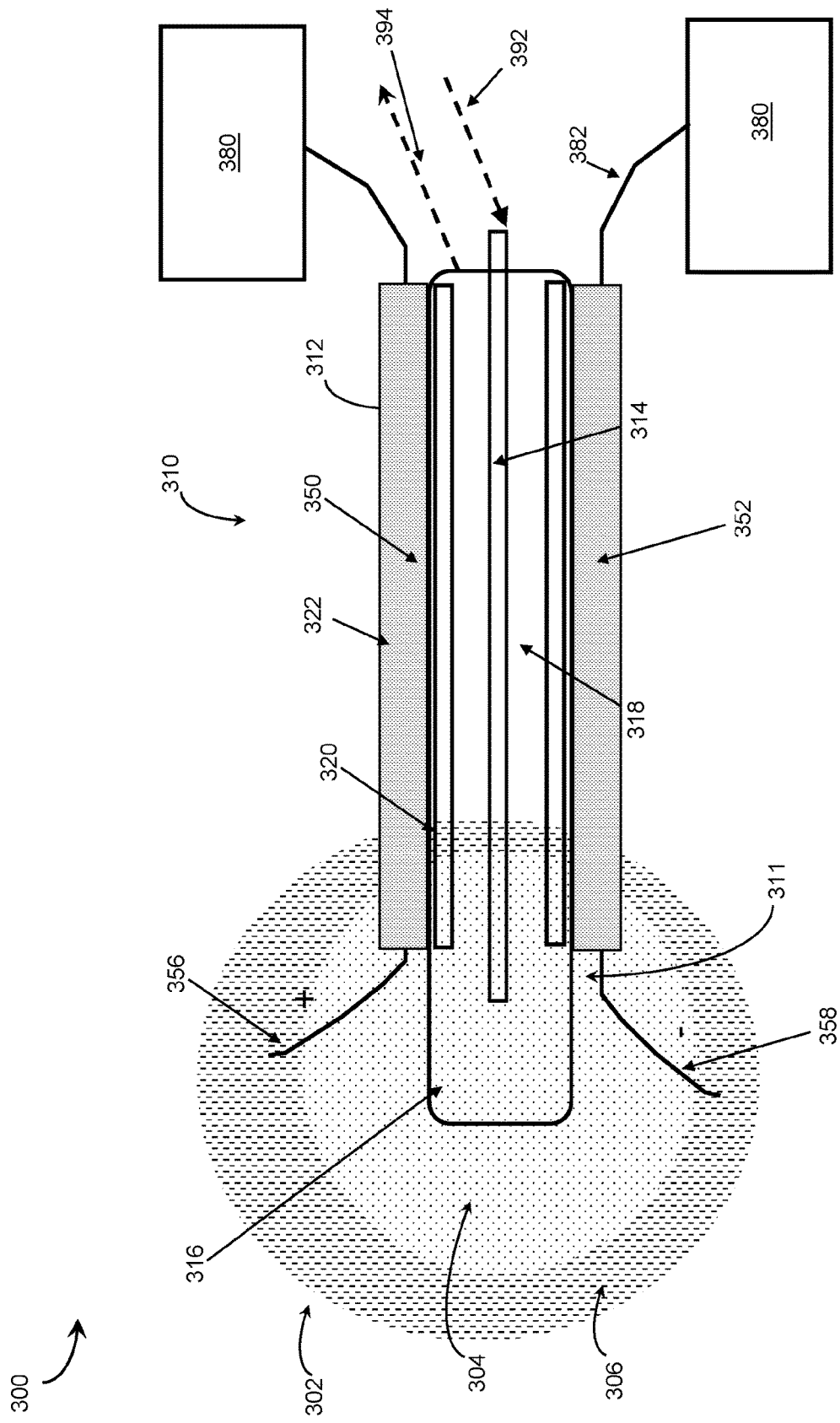
FIG. 7 is an embodiment of a device having one cryoprobe and two retractable electrode needles.

Shown in FIG. 7 is an embodiment of an injection device 300 that has a single cryoprobe 310. The elements of the injection device are similar to the previous embodiments, however the injection device 300 has a single cryoprobe 310. The cryoprobe 310 is capable of delivering both cold and electrical pulses to a target tissue 302 and has a first end 311, a second end 312, a central gas supply cannula 314 running between them and attached to a cryomachine 390 (not shown) that is a source of cooled gas pumped via a gas supply line 392 to the cryoprobe 310 and delivered to a cooling head 316 and removed by a gas return channel 318 concentrically surrounding and fluidly connected to the central gas supply cannula 314. A layer of thermal insulation 320 and a layer of electrical insulation 322 are also present.

One or two electrical pulse generators 380 (as shown in FIG. 7) are connected by wires 382 to the second end 312 of the cryoprobe 310. The wires 382 attach to a pair of wires 350, 352 that terminate in electrodes 356, 358 that exit the body of the cryoprobe and enter the tissue 302 alongside the cooling head 316. The wires 350, 352 are embedded in the electrical insulation layer 322, e.g., by piercing the electrical insulation layer 322 or by insertion into channels that run the length of the electrical insulation layer 322. The wires 350, 352 and electrodes 356, 358 can attach to each other, respectively, or in some embodiments the positive wire 350 and positive electrode 356 are the same continuous wire and the negative wire 352 and negative electrode 358 are the same continuous wire.

The electrodes 356, 358 are shaped such that when extended into the tissue 302 the electrodes curve away from the body of the cryoprobe 310. When retracted, the electrodes 356, 358 are held in a linear shape to better align with the body of the cryoprobe. The electrodes 356, 358 can be formed of e.g., nickel titanium (also known as nitinol). The curvature of the electrodes 356, 358 allows the user to extend the resulting RE zone 306 beyond the cryolesion zone 304. The user can extend the electrodes 356, 358 and transmit electric pulses before, during, or after the cryotherapy treatment.

Figure 8A:
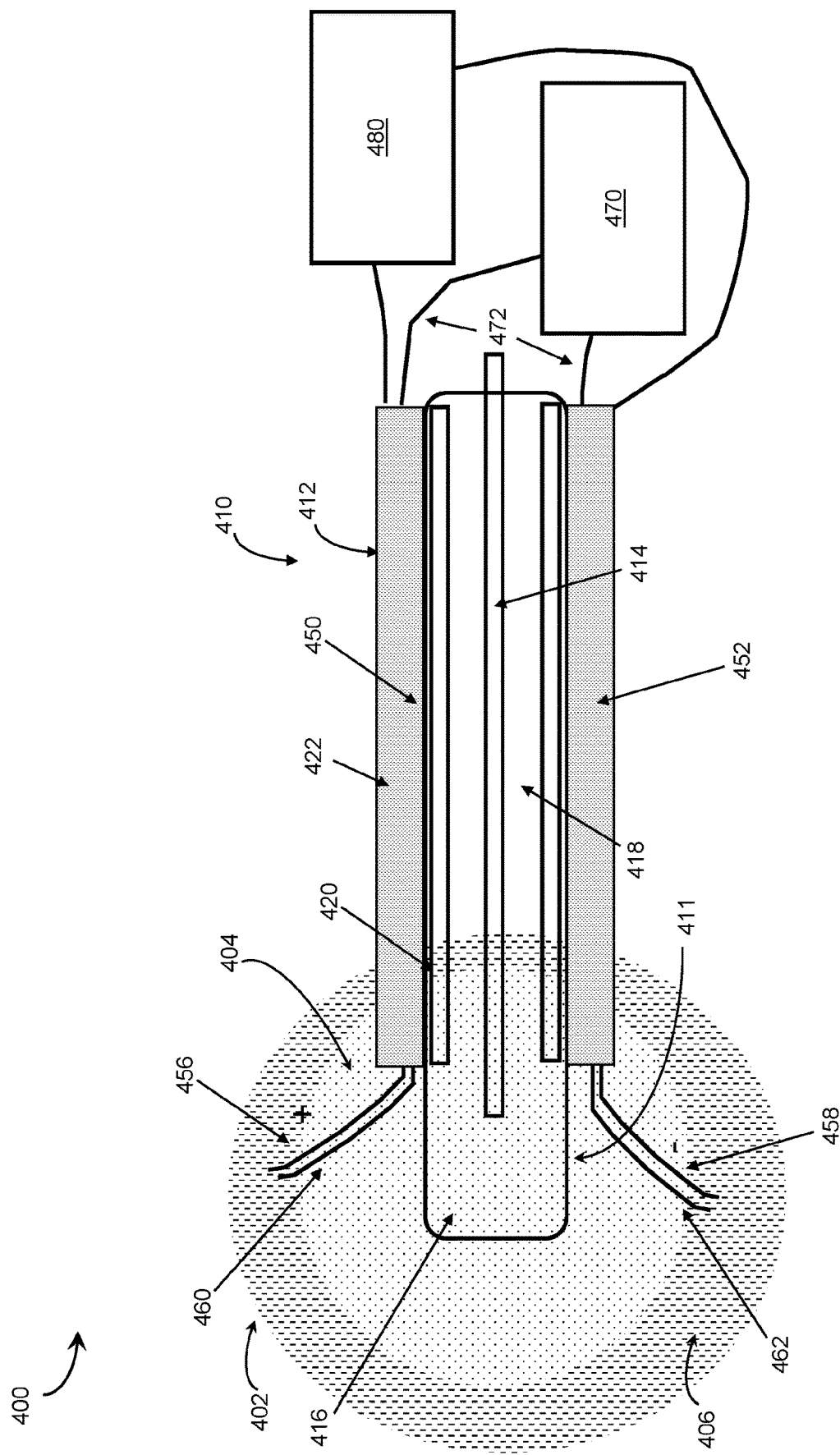
FIG. 8A is an embodiment of a device having one cryoprobe and two retractable electrode needles configured to inject plasmids.
Figure 8B:
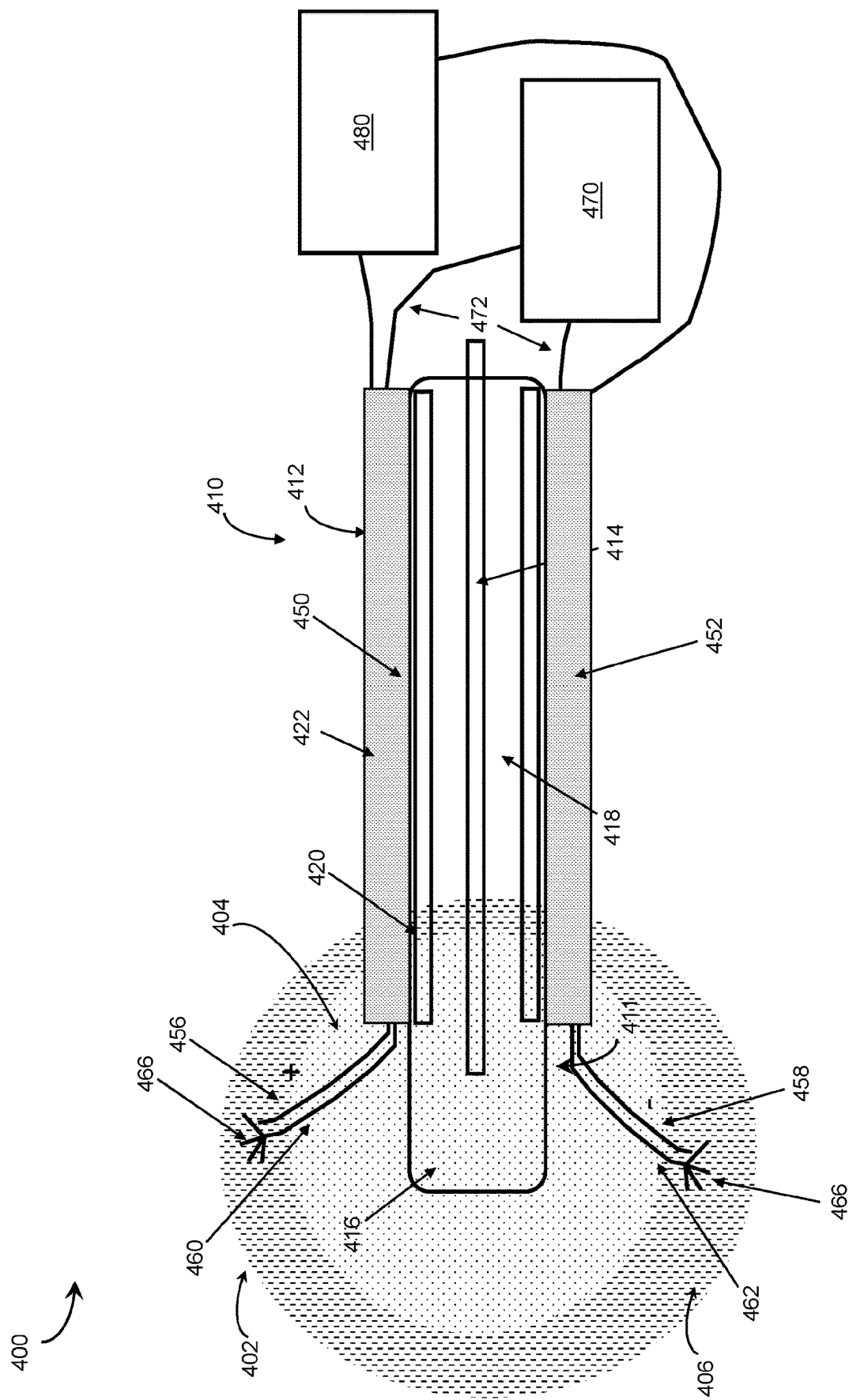
FIG. 8B is an embodiment of a device having one cryoprobe and retractable electrode needles configured to inject plasmids.

FIG. 8A shows an injection device 400 similar to that of FIG. 7 (with reference labels referring to the same elements as in FIG. 7 but raised by 100). However injection device 400 is capable of injecting plasmids into tissue 402 as well as administering electrotherapy and cryotherapy. The cryoprobe 410 has needles 460, 462 that extend approximately parallel with electrodes 456, 458 and are inserted into tissue 402. At the second end 412 of the cryoprobe, the needles 460, 462 are fluidly connected to tubes 472 which receives fluid from a fluid reservoir 470. For example, the fluid reservoir 470 can be a syringe. Fluid, e.g., plasmids, inside the fluid reservoir 470 can therefore be administered to the tissue 402. The needles 460, 462 are fully or partially retractable into the body of the cryoprobe 410 as are the electrodes 456, 458. The needles 460, 462 and electrodes 456, 458 can be retracted simultaneously or independently of each other. The needles 460, 462 are also repositionable within the tissue 402. In some embodiments, shown in FIG. 8B, the needles 460, 462 can have multiple tines 466. Multiple tines 466 can allow the user greater control over the spread and distribution of the injected materials or medications in a more quickly and precisely controllable pattern and at a specific distance from the central probe.

Figure 9:
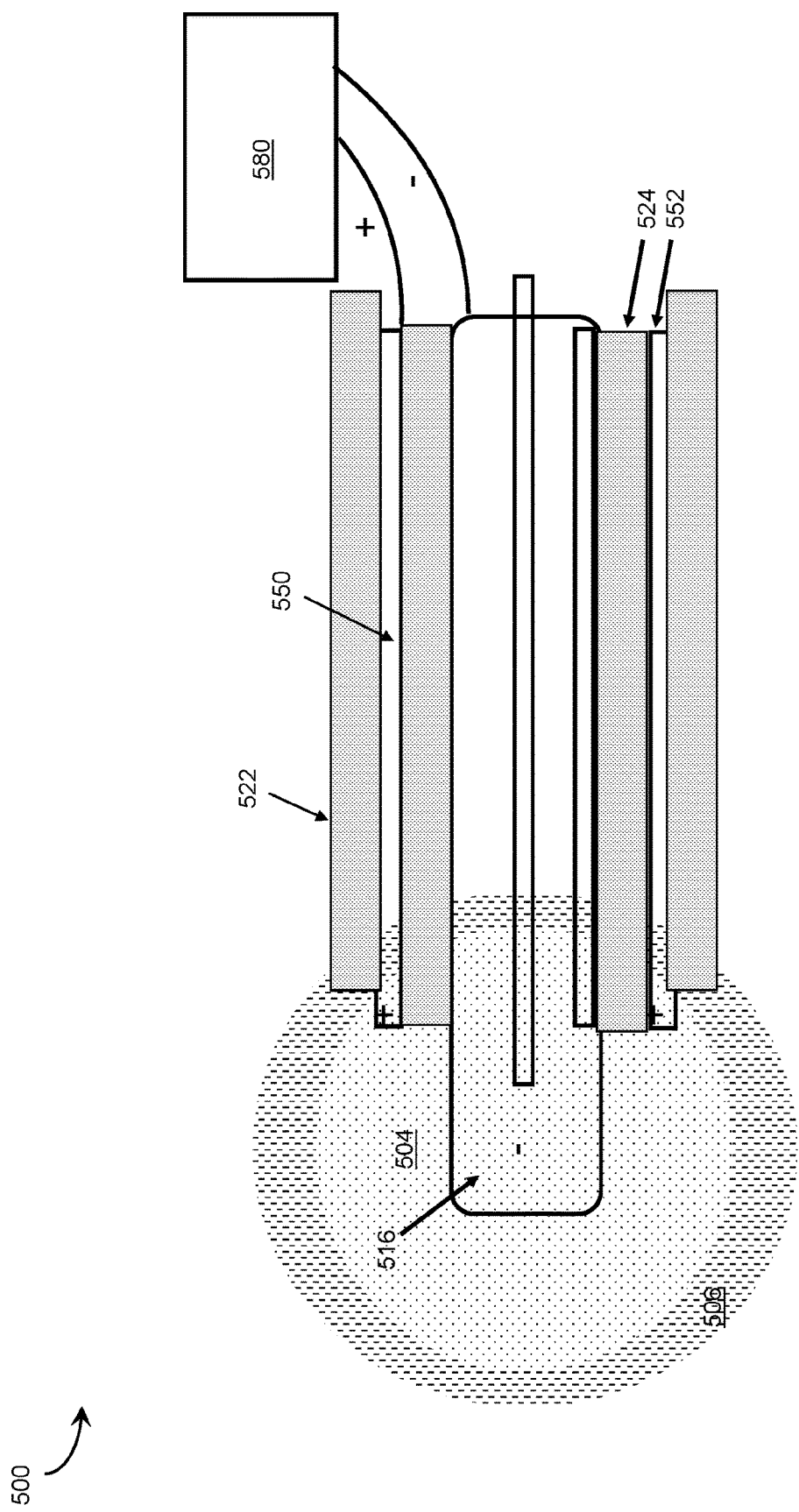
FIG. 9 is an embodiment of a device having one cryoprobe and two electrodes on the single cryoprobe.

FIG. 9 shows a cryoprobe 500 with two layers of electrical insulation 522, 524. Wires or electrical conduits 550, 552 are sandwiched between the two layers of electrical insulation 522, 524 and carry positive charge from the electric pulse generator 580. The body of the cryoprobe 500 terminates in the cooling head 516 and acts as an electrical conduit for the negative charge generated by the electrical pulse generator 580. Each of the two layers of electrical insulation 522, 524 is independently positionable and retractable.

Figure 10:
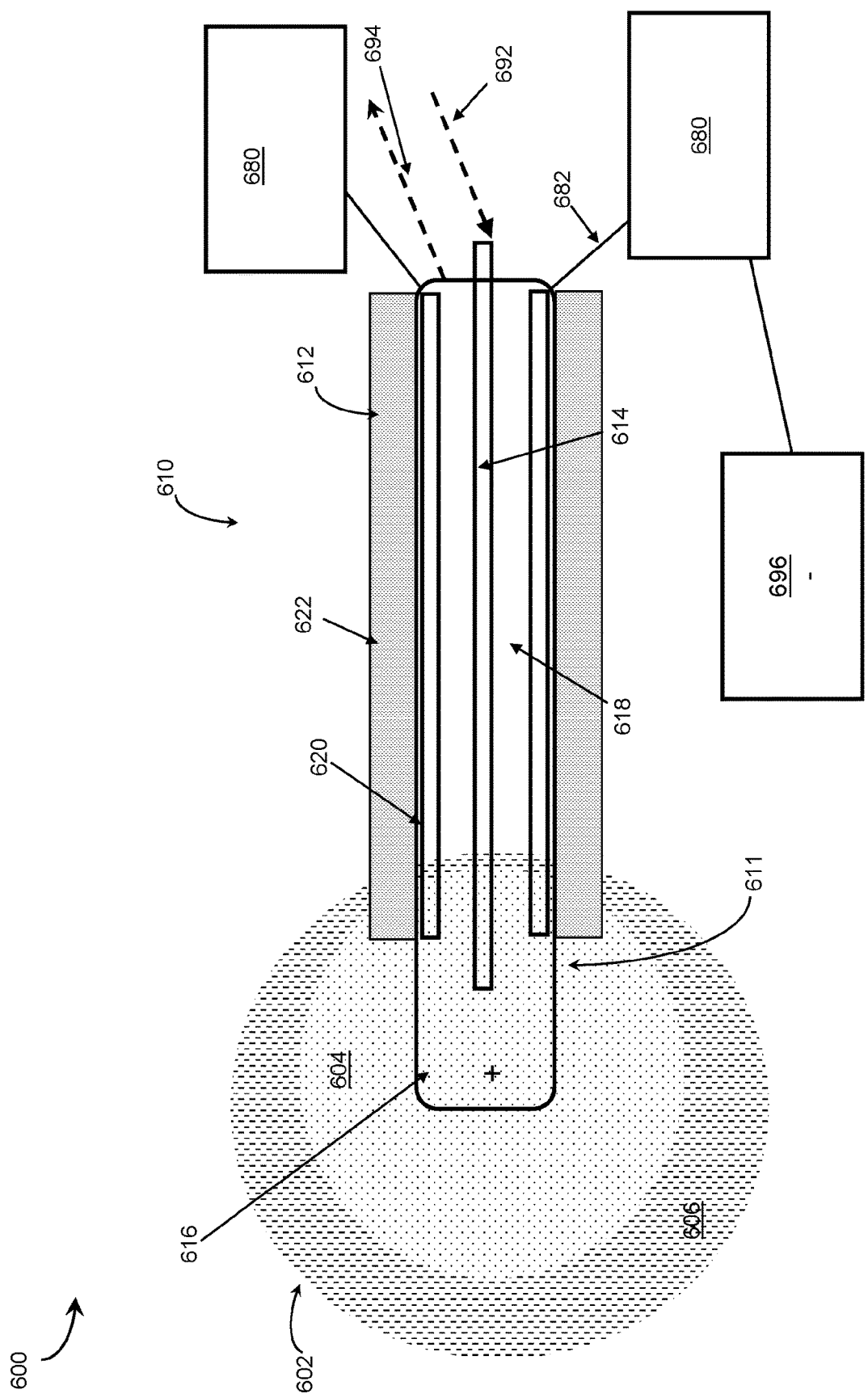
FIG. 10 is an embodiment of a device having one cryoprobe electrode and one indifferent electrode.

Shown in FIG. 10 is an embodiment of an injection device 600 that has a single cryoprobe 610. The elements of the injection device are similar to the previous embodiments, however the injection device 600 has a single cryoprobe 610 that works with an indifferent electrode 696, which is a remote electrode placed either upon a single limb or connected with the central terminal and paired with an exploring electrode of cryorobe 610. The cryoprobe 610 is capable of delivering both cold and electrical pulses to a target tissue 602 and has a first end 611, a second end 612, and a central gas supply cannula 614 running between them and attached to a cryomachine 690 (not shown) that is a source of cooled gas pumped via a gas supply line 692 to the cryoprobe 610 and delivered to a cooling head 616 and removed by a gas return channel 618 concentrically surrounding and fluidly connected to the central gas supply cannula 614. A layer of thermal insulation 620 and a layer of electrical insulation 622 are also present. One or two electrical pulse generators 680 (as shown in FIG. 10) are connected by wires 682 to the second end 612 of the cryoprobe 610, and also to the indifferent electrode 696.

Figure 11:
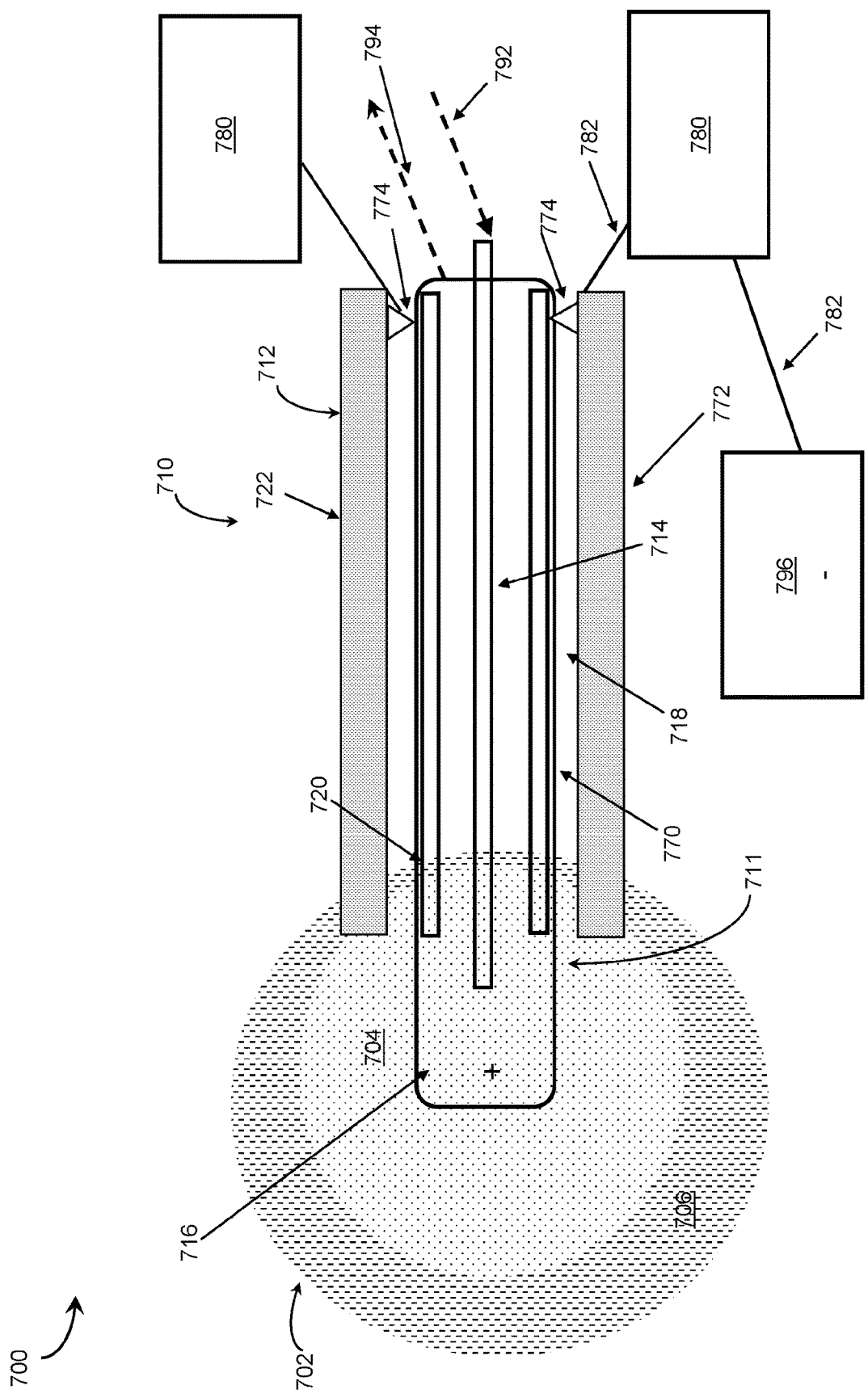
FIG. 11 is an embodiment of a device having a cryoprobe treatment portion detachable from an electric therapy delivery portion.

Referring to FIG. 11, an additional embodiment of an injection device 700 is described. The elements of the injection device 700 are similar to the previous embodiments. The injection device 700 has a single probe 710 that can be configured to work with an indifferent electrode 796. In some embodiments the injection device 700 includes a cryoprobe which is capable of delivering both cold and electrical pulses to a target tissue 702, and has a first end 711 and a second end 712.

Probe 710 is made of two different portions, a central portion 770 and concentric portion 772. The central portion has central gas supply cannula 714 running between the first and second ends of the probe 710 and is attached to a source of cooled gas pumped via a gas supply line 692 to the central portion 770 and delivered to a cooling head 716, and removed by a gas return channel 718 concentrically surrounding and fluidly connected to the central gas supply cannula 714. A layer of thermal insulation 720 surrounds the gas channels.

The concentric portion 772 surrounds the central portion 770, and is surrounded by a layer of electrical insulation 722. One or two electrical pulse generators 780 (two are shown in FIG. 11) are connected by wires 782 to the second end 712 of the probe 710, specifically at concentric portion 772, and also to the indifferent electrode 796. The concentric portion 772 is attachable to and removable from the central portion 770. Concentric portion 772 has the form of a sheath that surrounds the internal central portion 772 and the concentric portion 772 can be slid onto and off of the central portion 770 by repositioning the concentric portion 772 relative to the axial length of the central portion 770.

Electrical contacts 774 are included on the concentric portion 772, (e.g., on its inner surface). The electrical contacts 774 bring the wires 782 attached to the electrical pulse generator(s) 780 and indifferent electrode 796 into electric contact with an electrically conducting part of the central portion 770. If the central portion 770 is made of metal, or other conducting material, the electric impulses are thereby transmitted along the body of the central portion to the cooling head 716 to administer the electric therapy to the tissue 702. Alternatively, the central portion 770 can have wires configured to transmit current from the pulse generator(s) along the length of the central portion 770.

The embodiment shown in FIG. 11 is particularly advantageous. The concentric portion 772 can be manufactured separately from the central portion 770. For example, central portion 770 can be a complete cryoprobe that is traditionally used in such therapies. Attaching the concentric portion 772 to the outside of the central portion 770 increases the functionality of the probe, allowing the previously single-use cryoprobe to additionally provide electric RF-EMB treatment capability.

The embodiment of FIG. 11 allows a user to perform combined electric RF-EMB treatment and cryotherapy in a highly precise manner, and with increased flexibility. The probe 710 can be inserted into the tumor or target tissue 702 as desired. Only the concentric portion 722, the central portion 772, or both the portions can be positioned as desired. In one embodiment, the user inserts the probe 710 with bother inner and outer portions, and performs the desired therapeutic protocol. The user then can remove the central portion 770 from the tissue 702 by sliding it out of the concentric portion 772 while the concentric portion 772 remains in place. The user then can replace the removed central portion with a different central portion (e.g., a needle for delivering plasmids as described above, a tool that has neither cryo nor electricity-delivering capability such as a measurement tool, an acidity sensing or bioactive device, a tissue collection tool, a biopsy tool, or a hypothermia probe). The concentric portion 772 remaining in place allows the user to insert the new central portion with high accuracy, precisely returning to the previous location of the first end of the central portion 772 before it was removed from the tissue 702.

In some embodiments, the concentric portion 772 of the probe 710 can be used in conjunction with tools other than a probe inserted within the concentric portion 772. Once in place, the concentric portion 772 acts as a guidance device so that a different tool is inserted into the precise same location with the benefit of the next tool being placed in the same location as the prior tool. The replacement inner tool can be any tool that fits within concentric portion 772 (such a measurement tool). The replacement tool can be energized through the electric contacts 774 on the concentric portion 772.

In some embodiment, tools that replace the inner portion to work with concentric portion 772 can be tools that have corresponding electrical contacts on the body of the tool to mate with the electric contacts 774 on the centric probe portion 772. Such inner tools can be previously existing tools that are modified to have such electrical contacts, or tools designed to include such contacts. Additionally, each tool function can be used to cause a desired effect in the tissue 702, and depending on the characteristic of the replacement inner tool and the parameters used each tool can cause an effect in only a part of the tissue 702.

In some embodiments, probe 710 has a locking mechanism or alignment mechanism between the concentric portion 772 and the central portion 770 (e.g., a lever, spring, clip, or luer-type lock). Once the central portion 770 is inserted into the concentric portion 772, the locking mechanism keeps the inner and outer portions aligned and stationary relative to each other. In some embodiments, the probe 710 will only function once the locking mechanism between the inner and outer portions are engaged. For example, the user would have to twist the central portion 770 into engagement with a ridge on the concentric mechanism, and completing the movement would bring electrical contacts on the central portion into contact with the electrical contacts 774 of the concentric portion.

A number of embodiments of the invention have been described. Nevertheless, it will be understood that various modifications may be made without departing from the spirit and scope of the invention. For example, although two cryoprobes are shown in FIGS. 5 and 6, additional pairs of cryoprobes can be used as well. Additionally, although a single pair of wires is shown in FIG. 7, additional pairs of wires can be employed. In some embodiments the needles or tines 466 are configured to measure local pressure within the target tissue. Accordingly, other embodiments are within the scope of the following claims.

EXAMPLES

The invention is further described in the following examples, which do not limit the scope of the invention described in the claims.

Example 1

Treatment of Prostate Cancer in Patient A using Combination of Medications and Ablation A 72 year old male was diagnosed with prostate cancer (15 years ago). A radical prostatectomy was performed followed by secondary radiation therapy. Recurrent masses were visible in the pelvis (FIG. 1A) and nodal metastases closed off both ureters which lead to kidney failure and the necessity for a tube in the bladder for normal functionality.

Patient was subsequently treated with hormonal therapy using the basic and advanced $2^{nd}$ line cancer medicines. This treatment was unsuccessful and the cancer was categorized as Castrate resistant prostate cancer CRPC. Two further available chemotherapies (Taxotere and Carbezetaxal) were administered and unsuccessful, leading to Patient A being scheduled for Hospice care.

Figure 2:
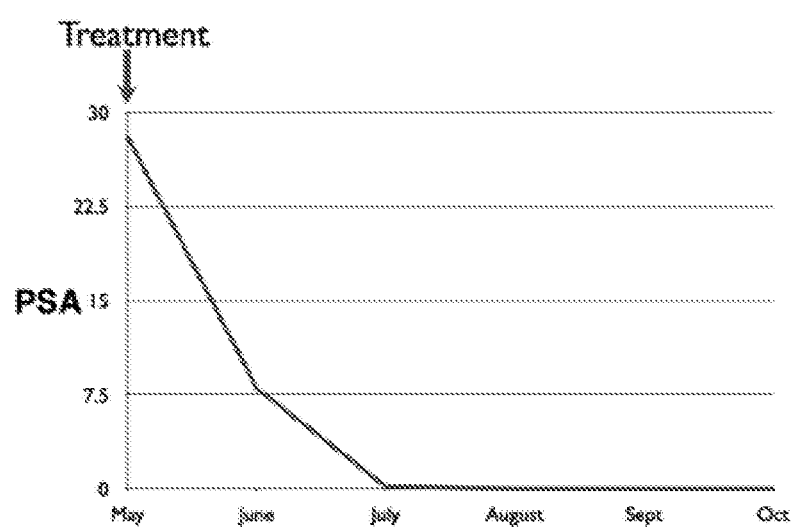
FIG. 2 is a graph illustrating the decline in prostrate-specific antigen (PSA) blood levels after the treatment described in Example 1.

A composition comprising a CTLA-4 inhibitor, a PD-1 inhibitor, and a cytokine was intra-tumorally administered to Patient A. Additionally the tumor was ablated to create an RF-EMB type lesion. Before this drug and ablation treatment, Patient A had a prostate-specific antigen (PSA) of approximately 28 (FIG. 2). 9 months after treatment, the PSA remains 0 with complete radiographic resolution of their disease (FIG. 1B).

Biopsies of the area showed no cancer but inflammatory cell infiltrates in the area of previous tumors are indicative of an immunologic response.

Example 2

Figures 3A, 3B:
FIGS. 3A-B are images of CT scans of Patient B's pelvic region before and after treatment with a CTLA-4 inhibitor, a PD-1 inhibitor, and a cytokine in addition to ablation. Arrows point to location of the initial tumor structure before treatment (FIG. 3A) and after treatment (FIG. 3B).

Treatment of Prostate Cancer in Patient B using Combination of Medications and Ablation A 65 year old male was diagnosed with prostate cancer. Masses were visible in the pelvis (FIG. 3A) of Patient B, and they had PSA levels of 130 and a Gleason score of 8. Metastases were identified in the lymph nodes.

Figure 4:
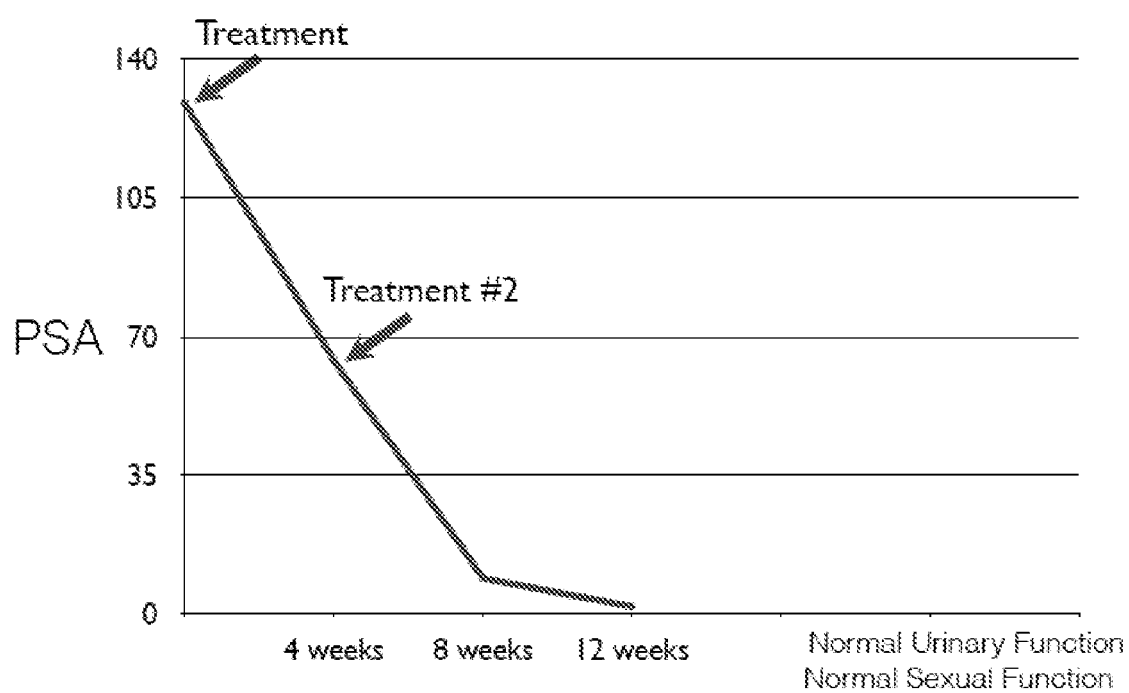
FIG. 4 is a graph illustrating the decline in PSA blood levels in Patient B after treatment.

Patient B was intra-tumorally administered the composition comprising a CTLA-4 inhibitor, a PD-1 inhibitor, and a cytokine; and the tumor was ablated to create an RF-EMB type lesion. After two rounds of this treatment Patient B has a PSA level of 1.8 and visible decrease in pelvic masses (FIG. 3B). 8 weeks after the second treatment, Patient B is reported to have normal urinary and sexual function in addition to lymph nodes back to a normal size (FIG. 4).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a tumor in a patient, comprising administering to the patient intratumorally a composition comprising a combination of at least two immune checkpoint inhibitors and at least one cytokine, each being prestin in the composition in therapeutically effecting amounts, and a pharmaceutically acceptable carrier, in an amount sufficient to treat the tumor, wherein the at least two checkpoint inhibitors are a CTLA-4 inhibitor and a PD-1 inhibitor, and wherein the at least one cytokine is GM-CSF; and
   ablating at least a portion of the tumor, thereby creating a zone of lesion, wherein the ablating is performed using a combination of radiofrequency electrical membrane breakdown (RF-EMB) and cryoablation, to thereby treat the tumor.

2. The method of claim 1, wherein ablating further comprises using RF-EMB type ablation, ultrasonic ablation, focused ultrasound ablation, ablation using photodynamic therapy, ablation using non-thermal shock waves, cavitation, other physical cell disruption, or any combination thereof.

3. The method of claim 2, wherein the portion of the tumor comprises cancer cells, and wherein the ablating is performed under conditions that disrupt cellular membranes of the cells and expose the intracellular components and membrane antigens of the cells.

4. The method of claim 3, wherein the ablation is performed such that intracellular components and membrane antigens of the cells are not denatured by the abaltion.

5. The method of claim 1, wherein the ablation is performed such that the amount of exposed intracellular components and membrane antigens of the cells is sufficient to stimulate the immune system.

6. The method of claim 1, wherein the ablation is performed such that the amount of exposed intracellular components and membrane antigens of the cells do not create immune tolerance.

7. The method of claim 1, further comprising administering subcutaneously to the patient a therapeutically effective amount of a second cytokine after ablating the tumor, wherein the second cytokine is the same or different from the first cytokine.

8. The method of claim 1, wherein the composition is injected in a single dose or in more than one dose.

9. The method of claim 1, wherein the compostion comprises the CTLA-4 inhibitor at a concentration of approximately 0.5 to 10 mg/ml, the PD-1 inhibitor at a concentration of approximatel 0.5 to 20 mg/ml, and the GM-CSF at a concentration of approximately 10 to 500 µg/ml.

10. The method of claim 1, wherein ablating is performed using a probe capable of RF-EMB.

11. The method of claim 1, wherein ablating is performed using a probe capable of RF-EMB and cryoablation.

12. The method of claim 1, wherein the compostion further comprises a cytokine selected from the group consisting of IL-6, IL-4, TNF, IFNγ, IFNα, or any combination thereof.

13. The method of claim 1, wherein the composition further comprises an inhibitor selected from the group consisting of an inhibitor of KIR, LAG-3, PD-L1, and any combination thereof.

14. The method of claim 1, wherein the CTLA-4 inhibitor is ipilimumab or tremelimumab and the PD-1 inhibitor is selected from the group consisting of pembrolizumab, nivolumab, pidilizumab, and MEDI 4736.

15. The method of claim 1, wherein the cryoablation comprises or consists of a single freeze cycle.

16. The method of claim 1, wherein the freeze is about 30 seonds long.

17. The method of claim 1, wherein the cryoablation is performed at temperature of about −30° C.

18. The method of claim 1, wherein the cryoablation is performed at a temperature of between −30° C.

19. A method of treating a tumor in a patient, comprising administering to the patient intratumorally a composition comprising a combination of at least two immune checkpoint inhibitors and at least one cytokine, each being present in the composition in therapeutically effective amounts, and a pharmaceutically acceptable carrier, in an amount sufficient to treat the tumor, wherein the at least two checkpoint inhibitors are a CTLA-4 inhibitor and a PD-1 inhibitor, and wherein the at least one cytokine is GM-CSF; and ablating at least a portion of the tumor, thereby creating a zone of lesion, wherein ablating is performed using cryoablation, wherein the cryoablation consists of a single freeze cycle, to thereby treat the tumor.

20. The method of claim 19, wherein the single freeze cycle is about 30 seconds long.

21. The method of claim 19, wherein the cryoablation is performed at a temperature of between −30° C. and −196° C.

22. The method of claim 21, wherein the cryoablation is performed at temperature of about −30° C.

23. The method of claim 19, wherein ablating further comprises using RFEMB, RF-EMB type ablation, ultrasonic ablation, focused ultrasound ablation, ablation using photodynamic thereapy, ablation using non-thermal shock waves, cavitation, other physical cell disruption, or any combination thereof.

24. The method of claim 19, wherein the portion of the tumor comprises cancer cells, and wherein the ablating is performed under conditions that disrupt cellular membranes of the cells and expose the intracellular components and membrane antigens of the cells.

25. The method of claim 19, wherein the ablation is performed such that intracellular compoentns and membrane antigens of the cells are not denatured by the ablation.

26. The method of claim 19, wherein the ablation is performed such that the amount of exposed intracellular compoents and membrane antigens of the cells is sufficient to stimulate the immune system.

27. The method of claim 19, wherein the ablation is performed such that the amount of exposed intracellular components and membrane antigens of the cells do not create immune tolerance.

28. The method of claim 1, in which the composition consists essentially of the two checkpoint inhibitors and the cytokine.

* * * * *

UNITED STATES PATENT AND TRADEMARK OFFICE
CERTIFICATE OF CORRECTION

PATENT NO. : 11,612,426 B2
APPLICATION NO. : 16/070072
DATED : March 28, 2023
INVENTOR(S) : Gary M. Onik, James A. Miessau and David Bostwick It is certified that error appears in the above-identified patent and that said Letters Patent is hereby corrected as shown below:

In the Claims

Column 26, Line 26, Claim 1, delete "prestin" and replace with --present--;

Column 26, Line 27, Claim 1, delete "effecting" and replace with --effective--;

Column 26, Line 49, Claim 4, delete "abaltion" and replace with --ablation--;

Column 26, Line 65, Claim 9, delete "compostion" and replace with --composition--;

Column 27, Line 1, Claim 9, delete "approximatel" and replace with --approximately--;

Column 27, Line 7, Claim 12, delete "compostion" and replace with --composition--;

Column 27, Line 22, Claim 16, delete "seonds" and replace with --seconds--;

Column 28, Line 11, Claim 23, delete "RFEMB" and replace with --RF-EMB--;

Column 28, Line 13, Claim 23, delete "thereapy" and replace with --therapy--;

Column 28, Line 23, Claim 25, delete "compoentns" and replace with --components--;

Column 28, Line 27, Claim 26, delete "compoents" and replace with --components--.

Signed and Sealed this
Fourth Day of July, 2023

Katherine Kelly Vidal
*Director of the United States Patent and Trademark Office*